US010980999B2

(12) United States Patent
Wong

(10) Patent No.: US 10,980,999 B2
(45) Date of Patent: Apr. 20, 2021

(54) PADDLE LEADS AND DELIVERY TOOLS, AND ASSOCIATED SYSTEMS AND METHODS

(71) Applicant: Nevro Corp., Redwood City, CA (US)

(72) Inventor: Mark Steven Wong, Redwood City, CA (US)

(73) Assignee: Nevro Corp., Redwood City, CA (US)

(*) Notice: Subject to any disclaimer, the term of this patent is extended or adjusted under 35 U.S.C. 154(b) by 126 days.

(21) Appl. No.: 15/915,339

(22) Filed: Mar. 8, 2018

(65) Prior Publication Data

US 2018/0256892 A1 Sep. 13, 2018

Related U.S. Application Data

(60) Provisional application No. 62/469,430, filed on Mar. 9, 2017.

(51) Int. Cl.
*A61N 1/05* (2006.01)
*A61N 1/04* (2006.01)
*A61N 1/06* (2006.01)
*A61N 1/36* (2006.01)

(52) U.S. Cl.
CPC ........... *A61N 1/0553* (2013.01); *A61N 1/048* (2013.01); *A61N 1/06* (2013.01); *A61N 1/36017* (2013.01); *A61N 1/36021* (2013.01); *A61N 1/36071* (2013.01)

(58) Field of Classification Search
CPC .......................... A61N 1/0553; A61B 17/3468
See application file for complete search history.

(56) References Cited

U.S. PATENT DOCUMENTS

| | | |
|---|---|---|
| 3,195,540 A | 7/1965 | Waller et al. |
| 3,724,467 A | 4/1973 | Avery et al. |
| 3,774,618 A | 11/1973 | Avery |
| 3,796,221 A | 3/1974 | Hagfors |
| 4,096,866 A | 6/1978 | Fischell |
| 4,136,703 A | 1/1979 | Wittkampf |
| 4,141,365 A | 2/1979 | Fischell et al. |

(Continued)

FOREIGN PATENT DOCUMENTS

| | | |
|---|---|---|
| CN | 101920065 A | 12/2010 |
| EP | 0158316 A2 | 10/1985 |

(Continued)

OTHER PUBLICATIONS

US 6,184,239 B1, 02/2001, Puskas (withdrawn)

(Continued)

*Primary Examiner* — George R Evanisko
(74) *Attorney, Agent, or Firm* — Perkins Coie LLP

(57) ABSTRACT

Paddle leads and delivery tools, and associated systems and methods are disclosed. A representative system is for use with a signal delivery paddle that is elongated along a longitudinal axis, and has a paddle length and a first cross-sectional area distribution that includes a first maxima. The system comprises a delivery tool including a proximal handle and a distal connection portion positioned to removably couple to the signal delivery paddle. The paddle and the delivery tool together have a combined second cross-sectional area distribution along the length of the paddle, with a second maxima that is no greater than the first maxima.

12 Claims, 11 Drawing Sheets

(56) References Cited

U.S. PATENT DOCUMENTS 4,282,886 A 8/1981 King
4,285,347 A 8/1981 Hess
4,328,813 A 5/1982 Ray
4,355,224 A 10/1982 Mesick et al.
4,374,527 A 2/1983 Iversen
4,379,462 A 4/1983 Borkan et al.
4,383,532 A 5/1983 Dickhudt
4,414,986 A 11/1983 Dickhudt et al.
4,422,917 A 12/1983 Hayfield
4,432,377 A 2/1984 Dickhudt
4,462,401 A 7/1984 Burgio
4,462,402 A 7/1984 Burgio et al.
4,465,079 A 8/1984 Dickhudt
4,466,690 A 8/1984 Osypka
4,498,482 A 2/1985 Williams
4,515,168 A 5/1985 Chester et al.
4,538,624 A 9/1985 Tarjan
4,573,448 A 3/1986 Kambin
4,573,481 A 3/1986 Bullara
4,579,120 A 4/1986 MacGregor
4,603,696 A 8/1986 Cross, Jr. et al.
4,658,835 A 4/1987 Pohndorf
4,683,895 A 8/1987 Pohndorf
4,721,551 A 1/1988 Byers et al.
4,744,370 A 5/1988 Harris
4,744,371 A 5/1988 Harris
4,764,132 A 8/1988 Stutz, Jr.
4,796,642 A 1/1989 Harris
4,830,776 A 5/1989 Thompson
4,898,173 A 2/1990 Daglow et al.
4,919,653 A 4/1990 Martinez et al.
4,920,979 A 5/1990 Bullara
4,926,878 A 5/1990 Snedeker
4,934,367 A 6/1990 Daglow et al.
4,934,383 A 6/1990 Glumac
4,940,065 A 7/1990 Tanagho et al.
4,961,434 A 10/1990 Stypulkowski
4,979,511 A 12/1990 Terry, Jr.
5,000,194 A 3/1991 van den Honert et al.
5,007,902 A 4/1991 Witt
5,036,862 A 8/1991 Pohndorf
5,042,486 A 8/1991 Pfeiler et al.
5,046,511 A 9/1991 Maurer et al.
5,070,605 A 12/1991 Daglow et al.
5,072,458 A 12/1991 Suzuki
5,078,140 A 1/1992 Kwoh
5,081,990 A 1/1992 Deletis
5,121,754 A 6/1992 Mullett
5,129,404 A 7/1992 Spehr et al.
5,159,926 A 11/1992 Ljungstroem
5,179,962 A 1/1993 Dutcher et al.
5,190,529 A 3/1993 McCrory et al.
5,205,297 A 4/1993 Montecalvo et al.
5,211,165 A 5/1993 Dumoulin et al.
5,257,636 A 11/1993 White
5,265,608 A 11/1993 Lee et al.
5,273,053 A 12/1993 Pohndorf
5,306,236 A 4/1994 Blumenfeld et al.
5,314,458 A 5/1994 Najafi et al.
5,325,873 A 7/1994 Hirschi et al.
5,351,394 A 10/1994 Weinberg
5,351,687 A 10/1994 Kroll et al.
5,351,697 A 10/1994 Cheney et al.
5,354,326 A 10/1994 Comben et al.
5,360,441 A 11/1994 Otten
5,366,489 A 11/1994 Burgio et al.
5,375,596 A 12/1994 Twiss et al.
5,392,791 A 2/1995 Nyman et al.
5,425,367 A 6/1995 Shapiro et al.
5,458,629 A 10/1995 Baudino et al.
5,458,631 A 10/1995 Xavier
5,464,446 A 11/1995 Dreessen et al.
5,480,421 A 1/1996 Otten
5,496,363 A 3/1996 Burgio et al.
5,527,338 A 6/1996 Purdy
5,531,778 A 7/1996 Maschino et al.
5,562,722 A 10/1996 Racz et al.
5,578,074 A 11/1996 Mirigian
5,643,330 A 7/1997 Holsheimer et al.
5,669,882 A 9/1997 Pyles
5,690,117 A 11/1997 Gilbert
5,727,553 A 3/1998 Saad
5,728,148 A 3/1998 Bostrom et al.
5,730,628 A 3/1998 Hawkins
5,755,750 A 5/1998 Petruska et al.
5,759,471 A 6/1998 Malewicz
5,760,341 A 6/1998 Laske et al.
5,769,877 A 6/1998 Barreras, Sr.
5,843,148 A 12/1998 Gijsbers
5,846,226 A 12/1998 Urmey
5,848,126 A 12/1998 Fujita et al.
5,865,843 A 2/1999 Baudino
5,871,487 A 2/1999 Warner et al.
5,871,531 A 2/1999 Struble
5,895,416 A 4/1999 Barreras
5,902,236 A 5/1999 Iversen
5,927,277 A 7/1999 Baudino et al.
5,935,159 A 8/1999 Cross, Jr. et al.
5,957,912 A 9/1999 Heitzmann
5,957,965 A 9/1999 Moumane et al.
5,957,968 A 9/1999 Belden et al.
5,983,126 A 11/1999 Wittkampf
6,052,623 A 4/2000 Fenner et al.
6,055,456 A 4/2000 Gerber
6,066,165 A 5/2000 Racz
6,078,839 A 6/2000 Carson
6,104,960 A 8/2000 Duysens
6,106,460 A 8/2000 Panescu et al.
6,125,291 A 9/2000 Miesel et al.
6,129,742 A 10/2000 Wu et al.
6,134,459 A 10/2000 Roberts et al.
6,134,477 A 10/2000 Knuteson
6,144,866 A 11/2000 Miesel et al.
6,154,678 A 11/2000 Lauro
6,161,047 A 12/2000 King et al.
6,163,727 A 12/2000 Errico
6,175,769 B1 1/2001 Errico et al.
6,178,357 B1 1/2001 Gliner et al.
6,185,463 B1 2/2001 Baudino
6,192,278 B1 2/2001 Werner et al.
6,192,279 B1 2/2001 Barreras, Sr. et al.
6,198,952 B1 3/2001 Miesel
6,198,963 B1 3/2001 Haim et al.
6,205,356 B1 3/2001 Holcomb
6,205,359 B1 3/2001 Boveja
6,205,361 B1 3/2001 Kuzma et al.
6,210,417 B1 4/2001 Baudino et al.
6,214,016 B1 4/2001 Williams et al.
6,216,045 B1 4/2001 Black et al.
6,248,112 B1 6/2001 Gambale et al.
6,249,965 B1 6/2001 Bullara et al.
6,251,115 B1 6/2001 Williams et al.
6,263,230 B1 7/2001 Haynor et al.
6,273,877 B1 8/2001 West et al.
6,292,702 B1 9/2001 King et al.
6,296,631 B2 10/2001 Chow
6,300,359 B1 10/2001 Burgio
6,304,785 B1 10/2001 McCreery et al.
6,308,103 B1 10/2001 Gielen
6,309,401 B1 10/2001 Redko et al.
6,319,241 B1 11/2001 King et al.
6,321,104 B1 11/2001 Gielen et al.
6,321,123 B1 11/2001 Morris et al.
6,364,899 B1 4/2002 Dobak, III
6,366,815 B1 4/2002 Haugland et al.
6,371,943 B1 4/2002 Racz et al.
6,374,140 B1 4/2002 Rise
6,393,323 B1 5/2002 Sawan et al.
6,393,327 B1 5/2002 Scribner
6,397,108 B1 5/2002 Camps et al.
6,415,187 B1 7/2002 Kuzma et al.
6,429,217 B1 8/2002 Puskas
6,438,418 B1 8/2002 Swerdlow et al.
6,442,435 B2 8/2002 King et al.

(56) References Cited

U.S. PATENT DOCUMENTS 6,445,955 B1 9/2002 Michelson et al.
6,449,511 B1 9/2002 Mintchev et al.
6,456,874 B1 9/2002 Hafer et al.
6,463,328 B1 10/2002 John
6,464,682 B1 10/2002 Snoke
6,473,644 B1 10/2002 Terry, Jr. et al.
6,473,653 B1 10/2002 Schallhorn et al.
6,474,341 B1 11/2002 Hunter et al.
6,477,427 B1 11/2002 Stolz et al.
6,480,820 B1 11/2002 Clopton et al.
6,482,049 B1 11/2002 Swearingen
6,484,059 B2 11/2002 Gielen et al.
6,493,590 B1 12/2002 Wessman et al.
6,493,592 B1 12/2002 Leonard et al.
6,512,949 B1 1/2003 Combs et al.
6,516,226 B1 2/2003 Bishay et al.
6,516,807 B1 2/2003 Panescu et al.
6,522,927 B1 2/2003 Bishay et al.
6,522,929 B2 2/2003 Swing
6,522,932 B1 2/2003 Kuzma et al.
6,529,774 B1 3/2003 Greene
6,542,774 B2 4/2003 Hill et al.
6,542,780 B1 4/2003 Leonard
6,546,293 B2 4/2003 Errico et al.
6,549,797 B1 4/2003 Leonard et al.
6,549,810 B1 4/2003 Leonard et al.
6,549,812 B1 4/2003 Smits
6,553,264 B2 4/2003 Redko et al.
6,554,809 B2 4/2003 Ayes
6,556,868 B2 4/2003 Naritoku et al.
6,556,869 B1 4/2003 Leonard et al.
6,556,873 B1 4/2003 Smits
6,560,491 B1 5/2003 Leonard et al.
6,587,719 B1 7/2003 Barrett et al.
6,587,733 B1 7/2003 Cross, Jr. et al.
6,600,956 B2 7/2003 Maschino et al.
6,605,094 B1 8/2003 Mann et al.
6,609,029 B1 8/2003 Mann et al.
6,622,038 B2 9/2003 Barrett et al.
6,622,051 B1 9/2003 Bishay et al.
6,704,605 B2 3/2004 Soltis et al.
6,714,822 B2 3/2004 King et al.
6,718,209 B2 4/2004 Williamson et al.
6,718,211 B2 4/2004 Smits
6,721,604 B1 4/2004 Robinson et al.
6,725,096 B2 4/2004 Chinn et al.
6,733,500 B2 5/2004 Kelley et al.
6,735,471 B2 5/2004 Hill et al.
6,741,892 B1 5/2004 Meadows et al.
6,741,893 B2 5/2004 Smits
6,745,079 B2 6/2004 King
6,754,539 B1 6/2004 Erickson et al.
6,758,854 B1 7/2004 Butler et al.
6,805,676 B2 10/2004 Klint
6,836,687 B2 12/2004 Kelley et al.
6,842,647 B1 1/2005 Griffith et al.
6,847,845 B2 1/2005 Belden
6,871,098 B2 3/2005 Nuttin et al.
6,875,571 B2 4/2005 Crabtree et al.
6,895,276 B2 5/2005 Kast et al.
6,895,283 B2 5/2005 Erickson et al.
6,901,289 B2 5/2005 Dahl et al.
6,902,547 B2 6/2005 Aves et al.
6,907,293 B2 6/2005 Grill et al.
6,907,295 B2 6/2005 Gross et al.
6,907,299 B2 6/2005 Han
6,909,918 B2 6/2005 Stypulkowski
6,929,656 B1 8/2005 Lennox
6,934,589 B2 8/2005 Sundquist et al.
6,944,501 B1 9/2005 Pless
6,961,621 B2 11/2005 Krishnan et al.
6,970,747 B2 11/2005 Kokones et al.
6,980,863 B2 12/2005 van Venrooij et al.
6,981,314 B2 1/2006 Black et al.
6,993,384 B2 1/2006 Bradley et al.
6,993,390 B2 1/2006 Zappala
6,999,819 B2 2/2006 Swoyer et al.
6,999,820 B2 2/2006 Jordan
7,010,856 B2 3/2006 Suda et al.
7,020,531 B1 3/2006 Colliou et al.
7,022,109 B1 4/2006 Ditto
7,047,078 B2 5/2006 Boggs, II et al.
7,047,082 B1 5/2006 Schrom et al.
7,047,084 B2 5/2006 Erickson et al.
7,051,419 B2 5/2006 Schrom et al.
7,069,078 B2 6/2006 Houben
7,069,083 B2 6/2006 Finch et al.
7,072,719 B2 7/2006 Vinup et al.
7,090,661 B2 8/2006 Morris et al.
7,107,097 B2 9/2006 Stern et al.
7,107,104 B2 9/2006 Keravel et al.
7,110,827 B2 9/2006 Sage et al.
7,127,298 B1 10/2006 He et al.
7,130,691 B2 10/2006 Falci
7,130,696 B2 10/2006 Carter et al.
7,133,722 B2 11/2006 Hansen et al.
7,136,695 B2 11/2006 Pless et al.
7,142,919 B2 11/2006 Hine et al.
7,145,229 B2 12/2006 Maghribi et al.
7,146,222 B2 12/2006 Boling
7,146,224 B2 12/2006 King
7,149,585 B2 12/2006 Wessman et al.
7,153,279 B2 12/2006 Ayad
7,153,307 B2 12/2006 Scribner et al.
7,162,304 B1 1/2007 Bradley
7,164,944 B1 1/2007 Kroll et al.
7,164,951 B2 1/2007 Ries et al.
7,174,213 B2 2/2007 Pless
7,174,219 B2 2/2007 Wahlstrand et al.
7,181,288 B1 2/2007 Rezai et al.
7,182,726 B2 2/2007 Williams et al.
7,182,783 B2 2/2007 Trieu
7,184,838 B2 2/2007 Cross, Jr.
7,184,840 B2 2/2007 Stolz et al.
7,184,842 B2 2/2007 Seifert et al.
7,186,601 B2 3/2007 Fukunaga et al.
7,187,981 B2 3/2007 Tanaka
7,187,982 B2 3/2007 Seifert et al.
7,191,018 B2 3/2007 Gielen et al.
7,200,443 B2 4/2007 Faul
7,206,642 B2 4/2007 Pardo et al.
7,209,787 B2 4/2007 DiLorenzo
7,211,103 B2 5/2007 Greenberg et al.
7,212,867 B2 5/2007 Van Venrooij et al.
7,225,016 B1 5/2007 Koh
7,236,834 B2 6/2007 Christopherson et al.
7,244,150 B1 7/2007 Brase et al.
7,270,650 B2 9/2007 Morris et al.
7,282,033 B2 10/2007 Urmey
7,299,095 B1 11/2007 Barlow et al.
7,340,306 B2 3/2008 Barrett et al.
7,363,076 B2 4/2008 Yun et al.
7,363,089 B2 4/2008 Vinup et al.
7,379,776 B1 5/2008 Chitre et al.
7,383,090 B2 6/2008 O'Brien et al.
7,386,341 B2 6/2008 Hafer et al.
7,386,350 B2 6/2008 Vilims
7,393,351 B2 7/2008 Woloszko et al.
7,421,297 B2 9/2008 Giftakis et al.
7,425,142 B1 9/2008 Putz
7,450,992 B1 11/2008 Cameron
7,455,666 B2 11/2008 Purdy
7,460,913 B2 12/2008 Kuzma et al.
7,463,917 B2 12/2008 Martinez
7,486,991 B2 2/2009 Libbus et al.
7,493,159 B2 2/2009 Hrdlicka et al.
7,496,404 B2 2/2009 Meadows et al.
7,499,755 B2 3/2009 Cross, Jr.
7,500,985 B2 3/2009 Saadat
7,502,652 B2 3/2009 Gaunt et al.
7,546,164 B2 6/2009 King
7,580,753 B2 8/2009 Kim et al.
7,584,004 B2 9/2009 Caparso et al.
7,590,454 B2 9/2009 Garabedian et al.

(56) References Cited

U.S. PATENT DOCUMENTS 7,604,644 B2 10/2009 Schulte et al.
7,613,516 B2 11/2009 Cohen et al.
7,613,524 B2 11/2009 Jordan
7,616,988 B2 11/2009 Stahmann et al.
7,617,003 B2 11/2009 Caparso et al.
7,617,006 B2 11/2009 Metzler et al.
7,623,919 B2 11/2009 Goetz et al.
7,627,380 B2 12/2009 Podhajsky et al.
7,640,064 B2 12/2009 Swoyer
7,672,734 B2 3/2010 Anderson et al.
7,684,873 B2 3/2010 Gerber
7,689,284 B2 3/2010 Imran et al.
7,702,379 B2 4/2010 Avinash et al.
7,769,441 B2 8/2010 Foreman et al.
7,769,442 B2 8/2010 Shafer
7,769,472 B2 8/2010 Gerber
7,781,806 B2 8/2010 VanBuskirk et al.
7,797,057 B2 9/2010 Harris
7,805,188 B2 9/2010 Brushey
7,810,233 B2 10/2010 Krulevitch et al.
7,810,996 B1 10/2010 Giphart et al.
7,829,694 B2 11/2010 Kaemmerer
7,831,307 B1 11/2010 Moffitt
7,844,343 B2 11/2010 Wahlstrand et al.
7,853,330 B2 12/2010 Bradley et al.
7,860,568 B2 12/2010 Deininger et al.
7,881,806 B2 2/2011 Horrigan et al.
7,904,149 B2 3/2011 Gerber
7,922,738 B2 4/2011 Eichmann et al.
7,996,055 B2 8/2011 Hauck et al.
8,000,805 B2 8/2011 Swoyer et al.
8,010,207 B2 8/2011 Smits et al.
8,014,873 B2 9/2011 Jones et al.
8,019,439 B2 9/2011 Kuzma et al.
8,024,035 B2 9/2011 Dobak, III
8,036,756 B2 10/2011 Swoyer et al.
8,060,207 B2 11/2011 Wallace et al.
8,078,280 B2 12/2011 Sage
8,123,807 B2 2/2012 Kim
8,131,357 B2 3/2012 Bradley et al.
8,197,494 B2 6/2012 Jaggi et al.
8,224,459 B1 7/2012 Pianca et al.
8,255,057 B2 8/2012 Fang et al.
8,303,502 B2 11/2012 Washburn et al.
8,355,791 B2 1/2013 Moffitt
8,355,797 B2 1/2013 Caparso et al.
8,494,652 B2 7/2013 Cantlon et al.
8,548,601 B2 10/2013 Chinn et al.
8,634,934 B2 1/2014 Kokones et al.
8,676,331 B2 3/2014 Parker
8,731,671 B2 5/2014 Rodby et al.
8,805,519 B2 8/2014 Parker et al.
8,880,176 B2 11/2014 Boling
9,358,388 B2 6/2016 Parker et al.
2001/0014820 A1 8/2001 Gielen et al.
2001/0016765 A1 8/2001 Gielen et al.
2001/0023368 A1 9/2001 Black et al.
2001/0025192 A1 9/2001 Gerber et al.
2001/0027336 A1 10/2001 Gielen et al.
2001/0031989 A1 10/2001 Swing
2001/0053885 A1 12/2001 Gielen et al.
2002/0022872 A1 2/2002 Gielen et al.
2002/0022873 A1 2/2002 Erickson et al.
2002/0052640 A1 5/2002 Bigus et al.
2002/0107553 A1 8/2002 Hill et al.
2002/0111661 A1 8/2002 Cross et al.
2002/0128700 A1 9/2002 Cross
2002/0156513 A1 10/2002 Borkan
2002/0161417 A1 10/2002 Scribner
2002/0173718 A1 11/2002 Frisch et al.
2002/0177887 A1 11/2002 Krebs
2002/0198568 A1 12/2002 Hafer et al.
2003/0018365 A1 1/2003 Loeb
2003/0018367 A1 1/2003 DiLorenzo
2003/0032997 A1 2/2003 Pianca et al.
2003/0055476 A1 3/2003 Vinup et al.
2003/0062048 A1 4/2003 Gradon et al.
2003/0083697 A1 5/2003 Baudino et al.
2003/0083724 A1 5/2003 Jog et al.
2003/0088245 A1 5/2003 Woloszko et al.
2003/0097165 A1 5/2003 Krulevitch et al.
2003/0097166 A1 5/2003 Krulevitch et al.
2003/0114752 A1 6/2003 Henderson et al.
2003/0120150 A1 6/2003 Govari
2003/0136418 A1 7/2003 Behm
2003/0187483 A1 10/2003 Grey et al.
2003/0199948 A1 10/2003 Kokones et al.
2003/0199949 A1 10/2003 Pardo
2003/0199951 A1 10/2003 Pardo et al.
2003/0199952 A1 10/2003 Stolz et al.
2003/0199953 A1 10/2003 Stolz et al.
2003/0199962 A1 10/2003 Struble et al.
2003/0204206 A1 10/2003 Padua et al.
2003/0208247 A1 11/2003 Spinelli et al.
2003/0216792 A1 11/2003 Levin et al.
2003/0220677 A1 11/2003 Doan et al.
2003/0229387 A1 12/2003 Cross et al.
2003/0233134 A1 12/2003 Greenberg et al.
2004/0015133 A1 1/2004 Karim
2004/0015188 A1 1/2004 Coulter
2004/0015205 A1 1/2004 Whitehurst et al.
2004/0015206 A1 1/2004 Bishay et al.
2004/0024428 A1 2/2004 Barrett et al.
2004/0024439 A1 2/2004 Riso
2004/0024440 A1 2/2004 Cole
2004/0087877 A1 5/2004 Besz et al.
2004/0088009 A1 5/2004 Degroot
2004/0088021 A1 5/2004 Cameron et al.
2004/0088033 A1 5/2004 Smits et al.
2004/0088034 A1 5/2004 Smits et al.
2004/0093053 A1 5/2004 Gerber et al.
2004/0097803 A1 5/2004 Panescu
2004/0111139 A1 6/2004 McCreery
2004/0122475 A1 6/2004 Myrick et al.
2004/0127942 A1 7/2004 Yomtov et al.
2004/0138536 A1 7/2004 Frei et al.
2004/0152958 A1 8/2004 Frei et al.
2004/0162601 A1 8/2004 Smits
2004/0172085 A1 9/2004 Knudson et al.
2004/0172100 A1 9/2004 Humayun et al.
2004/0176683 A1 9/2004 Whitin et al.
2004/0186528 A1 9/2004 Ries et al.
2004/0186543 A1 9/2004 King et al.
2004/0186544 A1 9/2004 King
2004/0210290 A1 10/2004 Omar-Pasha
2004/0210291 A1 10/2004 Erickson et al.
2004/0215301 A1 10/2004 Lokhoff et al.
2004/0215305 A1 10/2004 Sage
2004/0215307 A1 10/2004 Michels et al.
2004/0236387 A1 11/2004 Fang et al.
2004/0243206 A1 12/2004 Tadlock
2004/0260356 A1 12/2004 Kara et al.
2005/0004417 A1 1/2005 Nelson et al.
2005/0004638 A1 1/2005 Cross
2005/0004639 A1 1/2005 Erickson
2005/0010260 A1 1/2005 Gerber
2005/0015128 A1 1/2005 Rezai et al.
2005/0020970 A1 1/2005 Gerber
2005/0021069 A1 1/2005 Feuer et al.
2005/0021119 A1 1/2005 Sage et al.
2005/0027325 A1 2/2005 Lahti et al.
2005/0027338 A1 2/2005 Hill
2005/0027339 A1 2/2005 Schrom et al.
2005/0027340 A1 2/2005 Schrom et al.
2005/0027341 A1 2/2005 Schrom et al.
2005/0033371 A1 2/2005 Sommer et al.
2005/0049486 A1 3/2005 Urquhart et al.
2005/0049648 A1 3/2005 Cohen et al.
2005/0049650 A1 3/2005 Nuttin et al.
2005/0049663 A1 3/2005 Harris et al.
2005/0049664 A1 3/2005 Harris et al.
2005/0065588 A1 3/2005 Zhao et al.
2005/0070969 A1 3/2005 Gerber
2005/0070974 A1 3/2005 Knudson et al.

(56) References Cited

U.S. PATENT DOCUMENTS

2005/0070982 A1 3/2005 Heruth et al.
2005/0070987 A1 3/2005 Erickson
2005/0075684 A1 4/2005 Phillips et al.
2005/0075702 A1 4/2005 Shafer
2005/0075707 A1 4/2005 Meadows et al.
2005/0085870 A1 4/2005 Goroszeniuk
2005/0090885 A1 4/2005 Harris et al.
2005/0096718 A1 5/2005 Gerber et al.
2005/0107753 A1 5/2005 Rezai et al.
2005/0107859 A1 5/2005 Daglow et al.
2005/0107861 A1 5/2005 Harris et al.
2005/0113878 A1 5/2005 Gerber
2005/0119713 A1 6/2005 Whitehurst et al.
2005/0131486 A1 6/2005 Boveja et al.
2005/0131506 A1 6/2005 Rezai et al.
2005/0137648 A1 6/2005 Cosendai et al.
2005/0137667 A1 6/2005 Omar-Pasha et al.
2005/0137668 A1 6/2005 Khan
2005/0138791 A1 6/2005 Black et al.
2005/0138792 A1 6/2005 Black et al.
2005/0165458 A1 7/2005 Boveja et al.
2005/0165465 A1 7/2005 Pianca et al.
2005/0171587 A1 8/2005 Daglow et al.
2005/0182420 A1 8/2005 Schulte et al.
2005/0182421 A1 8/2005 Schulte et al.
2005/0182422 A1 8/2005 Schulte et al.
2005/0182424 A1 8/2005 Schulte et al.
2005/0182425 A1 8/2005 Schulte et al.
2005/0187600 A1 8/2005 Hunter et al.
2005/0203599 A1 9/2005 Garabedian et al.
2005/0209665 A1 9/2005 Hunter et al.
2005/0209667 A1 9/2005 Erickson et al.
2005/0216070 A1 9/2005 Boveja et al.
2005/0222635 A1 10/2005 Krakovsky
2005/0222642 A1 10/2005 Przybyszewski et al.
2005/0222657 A1 10/2005 Wahlstrand et al.
2005/0222658 A1 10/2005 Hoegh et al.
2005/0222659 A1 10/2005 Olsen et al.
2005/0228221 A1 10/2005 Hirakawa
2005/0240229 A1 10/2005 Whitehurst et al.
2005/0246003 A1 11/2005 Black et al.
2005/0246004 A1 11/2005 Cameron et al.
2005/0283216 A1 12/2005 Pyles
2005/0288566 A1 12/2005 Levendusky et al.
2006/0004429 A1 1/2006 Mrva et al.
2006/0025832 A1 2/2006 O'Keeffe et al.
2006/0041277 A1 2/2006 Deem et al.
2006/0052765 A1 3/2006 Pyles et al.
2006/0085070 A1 4/2006 Kim
2006/0089691 A1 4/2006 Kaplan et al.
2006/0089692 A1 4/2006 Cross et al.
2006/0089695 A1 4/2006 Bolea et al.
2006/0089696 A1 4/2006 Olsen et al.
2006/0089697 A1 4/2006 Cross et al.
2006/0106440 A1 5/2006 Chandran et al.
2006/0111768 A1 5/2006 Wessman et al.
2006/0122654 A1 6/2006 Bradley et al.
2006/0127158 A1 6/2006 Olson et al.
2006/0161236 A1 7/2006 King
2006/0167525 A1 7/2006 King
2006/0168805 A1 8/2006 Hegland et al.
2006/0173262 A1 8/2006 Hegland et al.
2006/0200218 A1 9/2006 Wahlstrand
2006/0241725 A1 10/2006 Libbus et al.
2006/0247569 A1 11/2006 Bertrand et al.
2006/0247747 A1 11/2006 Olsen et al.
2006/0247748 A1 11/2006 Wahlstrand et al.
2006/0247749 A1 11/2006 Colvin
2006/0253182 A1 11/2006 King
2006/0259095 A1 11/2006 Wyler et al.
2006/0259110 A1 11/2006 Wallace et al.
2006/0264122 A1 11/2006 Aman et al.
2006/0265024 A1 11/2006 Goetz et al.
2006/0265037 A1 11/2006 Kuzma
2006/0271137 A1 11/2006 Stanton-Hicks
2007/0032836 A1 2/2007 Thrope et al.
2007/0038052 A1 2/2007 Swoyer et al.
2007/0043403 A1 2/2007 Blamey et al.
2007/0048289 A1 3/2007 Grandjean
2007/0050004 A1 3/2007 Swoyer et al.
2007/0050005 A1 3/2007 Lauro
2007/0055332 A1 3/2007 Swoyer
2007/0088414 A1 4/2007 Campbell et al.
2007/0100386 A1 5/2007 Tronnes et al.
2007/0100391 A1 5/2007 Armstrong
2007/0100408 A1 5/2007 Gerber
2007/0106144 A1 5/2007 Squeri
2007/0106289 A1 5/2007 O'Sullivan
2007/0112404 A1 5/2007 Mann et al.
2007/0118198 A1 5/2007 Prager
2007/0135881 A1 6/2007 Vilims
2007/0149048 A1 6/2007 O'Brien et al.
2007/0150026 A1 6/2007 Bourget et al.
2007/0150036 A1 6/2007 Anderson
2007/0191709 A1 8/2007 Swanson
2007/0191903 A1 8/2007 Bruinstroop
2007/0191904 A1 8/2007 Libbus et al.
2007/0191909 A1 8/2007 Ameri et al.
2007/0203540 A1 8/2007 Goetz et al.
2007/0208394 A1 9/2007 King et al.
2007/0213795 A1 9/2007 Bradley et al.
2007/0249901 A1 10/2007 Ohline et al.
2007/0255364 A1 11/2007 Gerber et al.
2007/0255365 A1 11/2007 Gerber et al.
2007/0255366 A1 11/2007 Gerber et al.
2007/0255367 A1 11/2007 Gerber et al.
2007/0255370 A1 11/2007 Bonde et al.
2007/0255371 A1 11/2007 Bonde et al.
2007/0260290 A1 11/2007 Hara et al.
2007/0261115 A1 11/2007 Gerber et al.
2008/0039738 A1 2/2008 Dinsmoor et al.
2008/0058875 A1 3/2008 Greenberg et al.
2008/0097475 A1 4/2008 Jaggi et al.
2008/0103569 A1 5/2008 Gerber
2008/0103572 A1 5/2008 Gerber
2008/0103576 A1 5/2008 Gerber
2008/0103578 A1 5/2008 Gerber
2008/0103579 A1 5/2008 Gerber
2008/0114433 A1 5/2008 Sage
2008/0125833 A1 5/2008 Bradley et al.
2008/0132926 A1 6/2008 Eichmann et al.
2008/0140087 A1 6/2008 Barbagli
2008/0140152 A1 6/2008 Imran et al.
2008/0177339 A1 7/2008 Bolea et al.
2008/0183221 A1 7/2008 Burdulis
2008/0234791 A1 9/2008 Arle et al.
2008/0262430 A1 10/2008 Anderson et al.
2008/0275467 A1 11/2008 Liao et al.
2008/0300651 A1 12/2008 Gerber et al.
2008/0319311 A1 12/2008 Hamadeh
2009/0048638 A1 2/2009 Rey et al.
2009/0069803 A1 3/2009 Starkebaum
2009/0125060 A1 5/2009 Rivard et al.
2009/0132017 A1 5/2009 Erickson et al.
2009/0198306 A1 8/2009 Goetz et al.
2009/0204173 A1 8/2009 Fang et al.
2009/0204192 A1 8/2009 Carlton et al.
2009/0210029 A1 8/2009 Tsui
2009/0216306 A1 8/2009 Barker
2009/0248118 A1 10/2009 Bradley et al.
2009/0270940 A1 10/2009 Deininger et al.
2009/0299444 A1 12/2009 Boling
2009/0319013 A1 12/2009 Boling et al.
2010/0069736 A1 3/2010 Finneran et al.
2010/0094115 A1 4/2010 Pond, Jr. et al.
2010/0094116 A1 4/2010 Silverstein
2010/0114283 A1 5/2010 King
2010/0137938 A1* 6/2010 Kishawi ............... A61N 1/0551 607/46
2010/0137944 A1 6/2010 Zhu
2010/0137955 A1 6/2010 Milijasevic et al.
2010/0152538 A1 6/2010 Gleason et al.
2010/0204569 A1 8/2010 Burnside et al.
2010/0211135 A1 8/2010 Caparso et al.

(56) References Cited

U.S. PATENT DOCUMENTS

2010/0256696 A1 10/2010 Schleicher et al.
2010/0267265 A1 10/2010 Dilmaghanian
2010/0274312 A1 10/2010 Alataris et al.
2010/0274314 A1 10/2010 Alataris et al.
2010/0274315 A1 10/2010 Alataris et al.
2010/0274316 A1 10/2010 Alataris et al.
2010/0274326 A1 10/2010 Chitre
2010/0274336 A1 10/2010 Nguyen-Stella et al.
2010/0280570 A1 11/2010 Sturm et al.
2010/0286551 A1 11/2010 Harlev et al.
2010/0292769 A1 11/2010 Brounstein et al.
2010/0298905 A1 11/2010 Simon
2010/0305631 A1 12/2010 Bradley et al.
2010/0318165 A1 12/2010 Harris
2010/0324414 A1 12/2010 Harlev et al.
2010/0324570 A1 12/2010 Rooney et al.
2011/0009927 A1 1/2011 Parker et al.
2011/0031961 A1 2/2011 Durand et al.
2011/0046617 A1 2/2011 Thompson et al.
2011/0071593 A1 3/2011 Parker
2011/0106052 A1 5/2011 Chiang et al.
2011/0106100 A1 5/2011 Bischoff
2011/0160568 A1 6/2011 Seeley et al.
2011/0178573 A1 7/2011 Nguyen-Stella et al.
2011/0202097 A1 8/2011 Bonde et al.
2011/0224682 A1 9/2011 Westlund et al.
2011/0230943 A1 9/2011 Johnson et al.
2011/0245903 A1 10/2011 Schulte et al.
2012/0083709 A1 4/2012 Parker et al.
2012/0083856 A1 4/2012 Thacker
2012/0173946 A1 7/2012 Terry et al.
2012/0209285 A1 8/2012 Barker et al.
2012/0232626 A1 9/2012 Daglow
2013/0041445 A1 2/2013 Erickson et al.
2013/0066331 A1 3/2013 Chitre et al.
2013/0066411 A1 3/2013 Thacker et al.
2013/0096642 A1 4/2013 Wingeier
2013/0116754 A1 5/2013 Sharma et al.
2013/0261697 A1 10/2013 Parker
2013/0268037 A1 10/2013 Schulte et al.
2014/0031837 A1 1/2014 Perryman et al.
2014/0180305 A1 6/2014 Pianca
2014/0200627 A1 7/2014 Parker et al.
2014/0303685 A1 10/2014 Rosenberg et al.
2014/0343564 A1 11/2014 Feler et al.
2014/0343656 A1 11/2014 Wechter
2015/0005859 A1 1/2015 Thacker et al.
2015/0012077 A1 1/2015 Parker et al.
2015/0141787 A1 5/2015 Bonde
2015/0151114 A1* 6/2015 Black .................. A61N 1/0553 607/117
2015/0290461 A1 10/2015 Min
2016/0059006 A1 3/2016 Doan et al.
2016/0302827 A1 10/2016 Chitre et al.
2016/0354609 A1 12/2016 Parker
2016/0360993 A1 12/2016 Thacker et al.
2017/0281949 A1 10/2017 Thacker

FOREIGN PATENT DOCUMENTS

EP 2327446 A1 6/2011
WO WO-9003824 A1 4/1990
WO WO-2006045091 A2 4/2006
WO WO-2006055388 A2 5/2006
WO WO-2008094952 8/2008
WO WO-2009097224 A1 8/2009
WO WO-2009129329 A1 10/2009
WO WO-2011014570 A1 2/2011
WO WO-2012036925 A1 3/2012
WO WO-2012112428 A1 8/2012

OTHER PUBLICATIONS

Kulkarni et al., "A two-layered forward model of tissue for electrical; impedance tomography," Physiol Meas., 30(6); pp. 1-24, Jun. 2009.

Intrel® Model 7490 / 7491 Extensions for Spinal Cord Stimulation (SCS), Medtronic Neuro, Minneapolis, MN 1984, 9 pages.

International Search Report and Written Opinion for International Patent Application No. PCT/US2018/021488, dated Jun. 25, 2018, Applicant: Nevro Corp., 12 pages.

Kumar et al., "Spinal Cord Stimulation in Treatment of Chronic Benign Pain: Challenges in Treatment Planning and Present Status, a 22-Year Experience," Neurosurgery, vol. 58, No. 3, Mar. 2006, 16 pages.

Extended European Search Report and Written Opinion for European Patent Application No. 18763988.5, Applicant: Nevro Corp., dated Oct. 28, 2020, 8 pages.

* cited by examiner

PADDLE LEADS AND DELIVERY TOOLS, AND ASSOCIATED SYSTEMS AND METHODS

CROSS-REFERENCE TO RELATED APPLICATION

The present application claims priority to U.S. Provisional Application No. 62/469,430, filed Mar. 9, 2017 and incorporated herein by reference.

TECHNICAL FIELD

The present disclosure is directed to paddle leads and delivery tools, and associated systems and methods. In particular embodiments, the delivery tools are configured to have a low profile and to engage the paddle leads without requiring significant additional features and/or cross-sectional size increases for the paddle lead.

BACKGROUND

Neurological stimulators have been developed to treat pain, movement disorders, functional disorders, spasticity, cancer, cardiac disorders, and various other medical conditions. Implantable neurological stimulation systems generally have an implantable signal generator and one or more leads that deliver electrical pulses to neurological tissue and/or muscle tissue. For example, several neurological stimulation systems for spinal cord stimulation (SCS) have cylindrical leads that include a lead body with a circular cross-sectional shape and one or more conductive rings (i.e., contacts) spaced apart from each other at the distal end of the lead body. The conductive rings operate as individual electrodes and, in many cases, the SCS leads are implanted percutaneously through a needle inserted into the epidural space, with or without the assistance of a stylet.

In other clinical settings, the patient receives a paddle lead, which has flat electrodes and a larger, flattened profile, and which is implanted via a surgical procedure (e.g., a laminectomy or a laminotomy). An advantage of the paddle lead is that it is generally more stable than a percutaneous lead. An advantage of the percutaneous lead is that it is less invasive to implant.

In either of the above instances, the implanted electrodes are connected to the implantable signal generator. The signal generator applies electrical pulses to the electrodes, which in turn modify the function of the patient's nervous system, such as by altering the patient's responsiveness to sensory stimuli and/or altering the patient's motor-circuit output. In SCS therapy for the treatment of pain, the signal generator applies electrical pulses to the spinal cord via the electrodes. In conventional SCS therapy, electrical pulses are used to generate sensations (known as paresthesia) that mask or otherwise alter the patient's sensation of pain. For example, in many cases, patients report paresthesia as a tingling sensation that is perceived as less uncomfortable than the underlying pain sensation.

In contrast to traditional or conventional (i.e., paresthesia-based) SCS, a form of paresthesia-free SCS has been developed that uses therapy signal parameters that treat the patient's sensation of pain without generating paresthesia or otherwise using paresthesia to mask the patient's sensation of pain. This technique can use high frequency signals to produce improved patient outcomes without producing paresthesia.

Whether the practitioner delivers high frequency or low frequency signals, delivering the signals via a paddle can present challenges. For example, while the paddle tends to be stable once implanted, it may be difficult to adequately steer the paddle into its proper location. Accordingly, there remains a need for improving surgical paddles and the techniques used to implant them.

DETAILED DESCRIPTION

General aspects of the environments in which the disclosed technology operates are described below under Heading 1.0 ("Overview") with reference to FIGS. 1A and 1B. Particular embodiments of the technology are described further under Heading 2.0 ("Representative Embodiments") with reference to FIGS. 2-8.

1.0 Overview

Figure 1A:
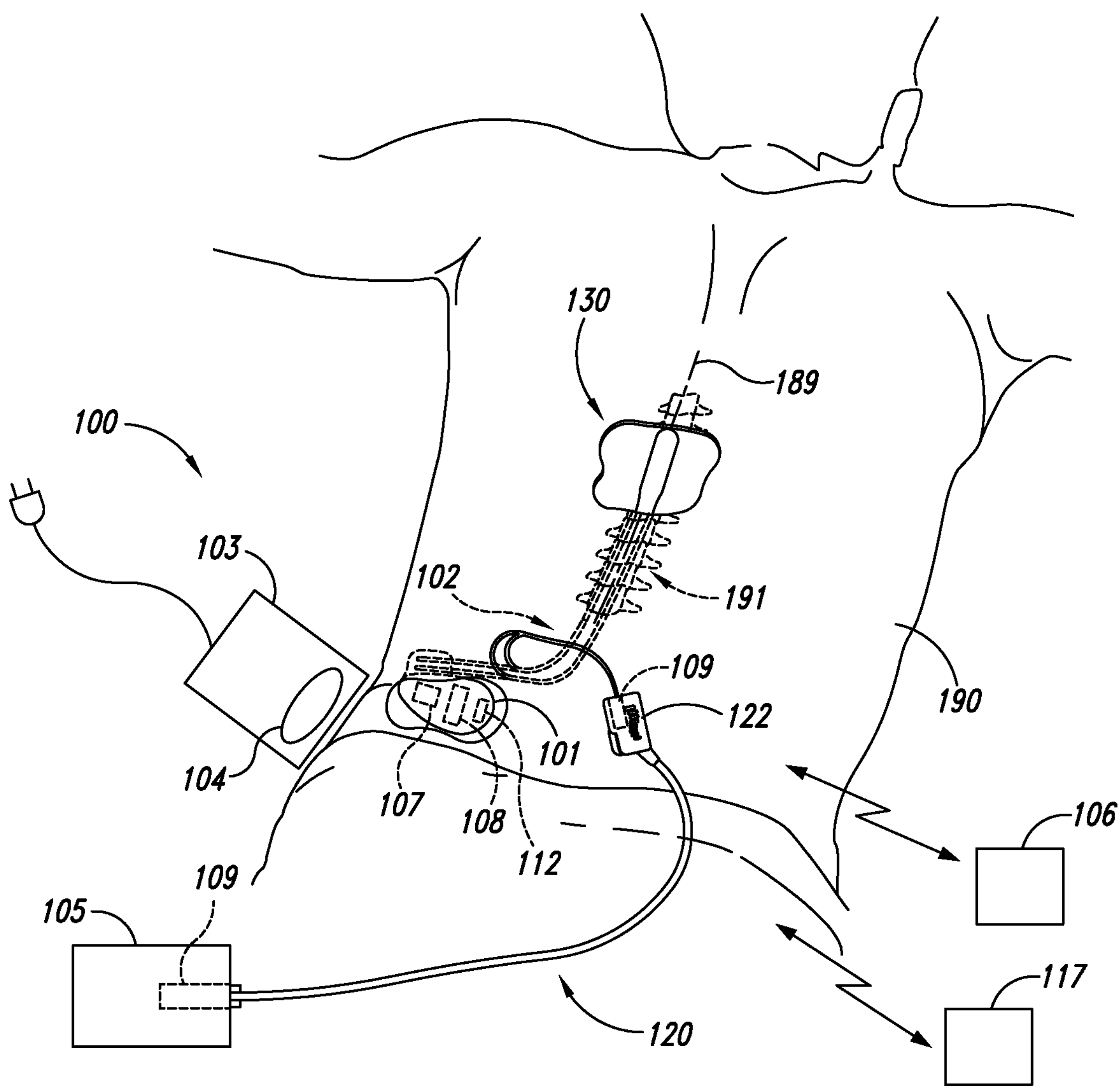
FIG. 1A is a partially schematic illustration of an implantable spinal cord modulation system positioned at the spine to deliver therapeutic signals in accordance with several embodiments of the present technology.

FIG. 1A schematically illustrates a representative patient therapy system 100 for providing relief from chronic pain and/or other conditions, arranged relative to the general anatomy of a patient's spinal column 191. The system 100 can include a signal generator 101 (e.g., an implanted or implantable pulse generator or IPG), which may be implanted subcutaneously within a patient 190 and coupled to one or more signal delivery elements or devices 130 (one is shown in FIG. 1A). The signal delivery device 130 may be implanted within the patient 190, typically at or near the patient's spinal cord midline 189. The signal delivery device 130 carries features for delivering therapy to the patient 190 after implantation. The signal generator 101 can be connected directly to the signal delivery device 130, or it can be coupled to the signal delivery device 130 via a signal link or lead extension 102. In an embodiment wherein the signal generator is external to the patient, the signal generator can deliver a signal to the signal delivery device 130 via a wireless link, such as an RF communication link.

In a further representative embodiment, the signal delivery device 130 can include a paddle body, which carries one or more electrodes that direct electrical signals into the patient's tissue e.g., to provide for therapeutic relief. The paddle body can be connected to one or more leads or lead legs that carry the electrical signals from the signal generator 101 to the electrodes. To insert the paddle body, the practitioner makes an incision, typically caudal to the implantation site, performs a laminectomy or a laminotomy to provide space in which to introduce the paddle body, and then inserts the paddle body epidurally into the spinal canal.

In a representative embodiment, the signal delivery device 130 may be implanted to straddle the spinal cord midline 189. In particular embodiments, the signal delivery device 130 may be implanted at a vertebral level ranging from, for example, about T8 to about T12 e.g., to treat low back and/or leg pain. In other embodiments, one or more signal delivery devices can be implanted at other vertebral levels, e.g., as disclosed in U.S. Patent Application Publication No. 2013/0066411, which is incorporated herein by reference in its entirety.

The signal generator 101 can transmit signals (e.g., electrical signals) to the signal delivery device 130 that up-regulate (e.g., excite) and/or down-regulate (e.g., block or suppress) target nerves. As used herein, and unless otherwise noted, the terms "modulate," "modulation," "stimulate," and "stimulation" refer generally to signals that have either type of the foregoing effects on the target nerves. The signal generator 101 can include a machine-readable (e.g., computer-readable) or controller-readable medium containing instructions for generating and transmitting suitable therapy signals. The signal generator 101 and/or other elements of the system 100 can include one or more processor(s) 107, memory unit(s) 108, and/or input/output device(s) 112. Accordingly, the process of providing modulation signals, providing guidance information for positioning the signal delivery devices 110, establishing battery charging and/or discharging parameters, establishing signal delivery parameters, and/or executing other associated functions can be performed by computer-executable instructions contained by, on, or in computer-readable media located at the pulse generator 101 and/or other system components. Further, the pulse generator 101 and/or other system components may include dedicated hardware, firmware, and/or software for executing computer-executable instructions that, when executed, perform any one or more methods, processes, and/or sub-processes described herein. The dedicated hardware, firmware, and/or software also serve as "means for" performing the methods, processes, and/or sub-processes described herein. The signal generator 101 can also include multiple portions, elements, and/or subsystems (e.g., for directing signals in accordance with multiple signal delivery parameters), carried in a single housing, as shown in FIG. 1A, or in multiple housings.

The signal generator 101 can also receive and respond to an input signal received from one or more sources. The input signals can direct or influence the manner in which the therapy, charging, parameter selection and/or other process instructions are selected, executed, updated, and/or otherwise performed. The input signals can be received from one or more sensors (e.g., an input device 112 shown schematically in FIG. 1A for purposes of illustration) that are carried by the signal generator 101 and/or distributed outside the signal generator 101 (e.g., at other patient locations) while still communicating with the signal generator 101. The sensors and/or other input devices 112 can provide inputs that depend on or reflect patient state (e.g., patient position, patient posture, and/or patient activity level), and/or inputs that are patient-independent (e.g., time). Still further details are included in U.S. Pat. No. 8,355,797, incorporated herein by reference in its entirety.

In some embodiments, the signal generator 101 and/or signal delivery device 130 can obtain power to generate the therapy signals from an external power source 103. In one embodiment, for example, the external power source 103 can by-pass an implanted signal generator (or eliminate the need for an implanted signal generator) and generate a therapy signal directly at the signal delivery device 130 (or via signal relay components). The external power source 103 can transmit power to the implanted signal generator 101 and/or directly to the signal delivery device 130 using electromagnetic induction (e.g., RF signals). For example, the external power source 103 can include an external coil 104 that communicates with a corresponding internal coil (not shown) within the implantable signal generator 101, the signal delivery device 130, and/or a power relay component (not shown). The external power source 103 can be portable for ease of use.

In another embodiment, the signal generator 101 can obtain the power to generate therapy signals from an internal power source, in addition to or in lieu of the external power source 103. For example, the implanted signal generator 101 can include a non-rechargeable battery or a rechargeable battery to provide such power. When the internal power source includes a rechargeable battery, the external power source 103 can be used to recharge the battery. The external power source 103 can in turn be recharged from a suitable power source (e.g., conventional wall power).

During at least some procedures, an external stimulator or trial modulator 105 can be coupled to the signal delivery device 130 during an initial procedure, prior to implanting the signal generator 101. For example, a practitioner (e.g., a physician and/or a company representative) can use the trial modulator 105 to vary the modulation parameters provided to the signal delivery device 130 in real time, and select optimal or particularly efficacious parameters. These parameters can include the location from which the electrical signals are emitted, as well as the characteristics of the electrical signals provided to the signal delivery device 130. In some embodiments, input is collected via the external stimulator or trial modulator and can be used by the clinician to help determine what parameters to vary. In a typical process, the practitioner uses a cable assembly 120 to temporarily connect the trial modulator 105 to the signal delivery device 130. The practitioner can test the efficacy of the signal delivery device 130 in an initial position. The practitioner can then disconnect the cable assembly 120 (e.g., at a connector 122), reposition the signal delivery device 130, and reapply the electrical signals. This process can be performed iteratively until the practitioner obtains the desired position for the signal delivery device 130. Optionally, the practitioner may move the partially implanted signal delivery device 130 without disconnecting the cable assembly 120. Furthermore, in some embodiments, the iterative process of repositioning the signal delivery device 130 and/or varying the therapy parameters may not be performed. In still further embodiments, the trial procedure described above can be modified. For example, the patient may receive a percutaneous lead during the trial procedure (to determine if the patient responds to the therapy) and a permanently implanted paddle when receiving the implanted pulse generator 101.

The signal generator 101, the lead extension 102, the trial modulator 105 and/or the connector 122 can each include a receiving element 109 for connection to other system components. Accordingly, the receiving elements 109 can be patient implantable elements, or the receiving elements 109 can be integral with an external patient treatment element, device or component (e.g., the trial modulator 105 and/or the connector 122). The receiving elements 109 can be configured to facilitate a simple coupling and decoupling procedure between the signal delivery device 130, the lead extension 102, the pulse generator 101, the trial modulator 105 and/or the connector 122. The receiving elements 109 can be at least generally similar in structure and function to those described in U.S. Patent Application Publication No. 2011/0071593, incorporated by reference herein in its entirety.

After the signal delivery device 130 is implanted, the patient 190 can receive therapy via signals generated by the trial modulator 105, generally for a limited period of time. During this time, the patient wears the cable assembly 120 and the trial modulator 105 outside the body. Assuming the trial therapy is effective or shows the promise of being effective, the practitioner then replaces the trial modulator 105 with the implanted signal generator 101, and programs the signal generator 101 with therapy programs selected based on the experience gained during the trial period. Once the implantable signal generator 101 has been positioned within the patient 190, the therapy programs provided by the signal generator 101 can still be updated remotely via a wireless physician's programmer 117 (e.g., a physician's laptop, a physician's remote or remote device, etc.) and/or a wireless patient programmer 106 (e.g., a patient's laptop, patient's remote or remote device, etc.). Generally, the patient 190 has control over fewer parameters than does the practitioner. For example, the capability of the patient programmer 106 may be limited to starting and/or stopping the signal generator 101, and/or adjusting the signal amplitude. The patient programmer 106 may be configured to accept pain relief input as well as other variables, such as medication use.

In any of the foregoing embodiments, the parameters in accordance with which the signal generator 101 provides signals can be adjusted during portions of the therapy regimen. For example, the frequency, amplitude, pulse width, and/or signal delivery location can be adjusted in accordance with a pre-set therapy program, patient and/or physician inputs, and/or in a random or pseudorandom manner. Such parameter variations can be used to address a number of potential clinical situations. Certain aspects of the foregoing systems and methods may be simplified or eliminated in particular embodiments of the present disclosure. Further aspects of these and other expected beneficial results are detailed in U.S. Patent Application Publication Nos. 2010/0274314; 2009/0204173; and 2013/0066411 (all incorporated elsewhere herein by reference) and U.S. Patent Application Publication No. 2010/0274317, which is incorporated herein by reference in its entirety.

Figure 1B:
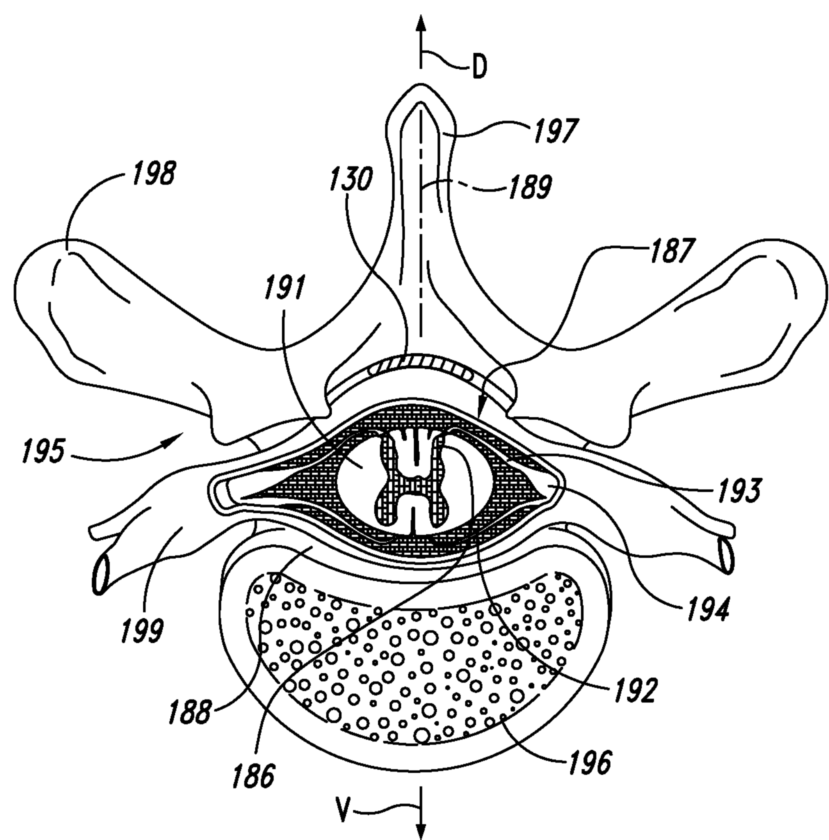
FIG. 1B is a partially schematic, cross-sectional illustration of a patient's spine, illustrating a representative location for an implanted signal delivery device configured in accordance with an embodiment of the present technology.

FIG. 1B is a cross-sectional illustration of the spinal cord 191 and an adjacent vertebra 195 (based generally on information from Crossman and Neary, "Neuroanatomy," 1995 (published by Churchill Livingstone)), along with a signal delivery device 130 implanted at a representative location.

The spinal cord 191 is situated within a vertebral foramen 188, between a ventrally located ventral body 196 and a dorsally located transverse process 198 and spinous process 197. Arrows V and D identify the ventral and dorsal directions, respectively. The spinal cord 191 itself is located within the dura mater 199, which also surrounds portions of the nerves exiting the spinal cord 191, including the ventral roots 192, dorsal roots 193 and dorsal root ganglia 194. The dorsal roots 193 enter the spinal cord 191 at the dorsal root entry zone 187, and communicate with dorsal horn neurons located at the dorsal horn 186. The signal delivery device 130 can be positioned over the spinal cord midline 189 and can have a curved shape (in cross-section) to fit over the spinal cord 191. The signal delivery device 130 can also be flexible in both lateral and axial directions so as to conform to the patient's individual physiology. In other embodiments, the signal delivery device 130 can be positioned at other locations, e.g., toward the outer edge of the dorsal root entry zone 187 or at the dorsal root ganglia 194.

2.0 Representative Embodiments

Figure 2:
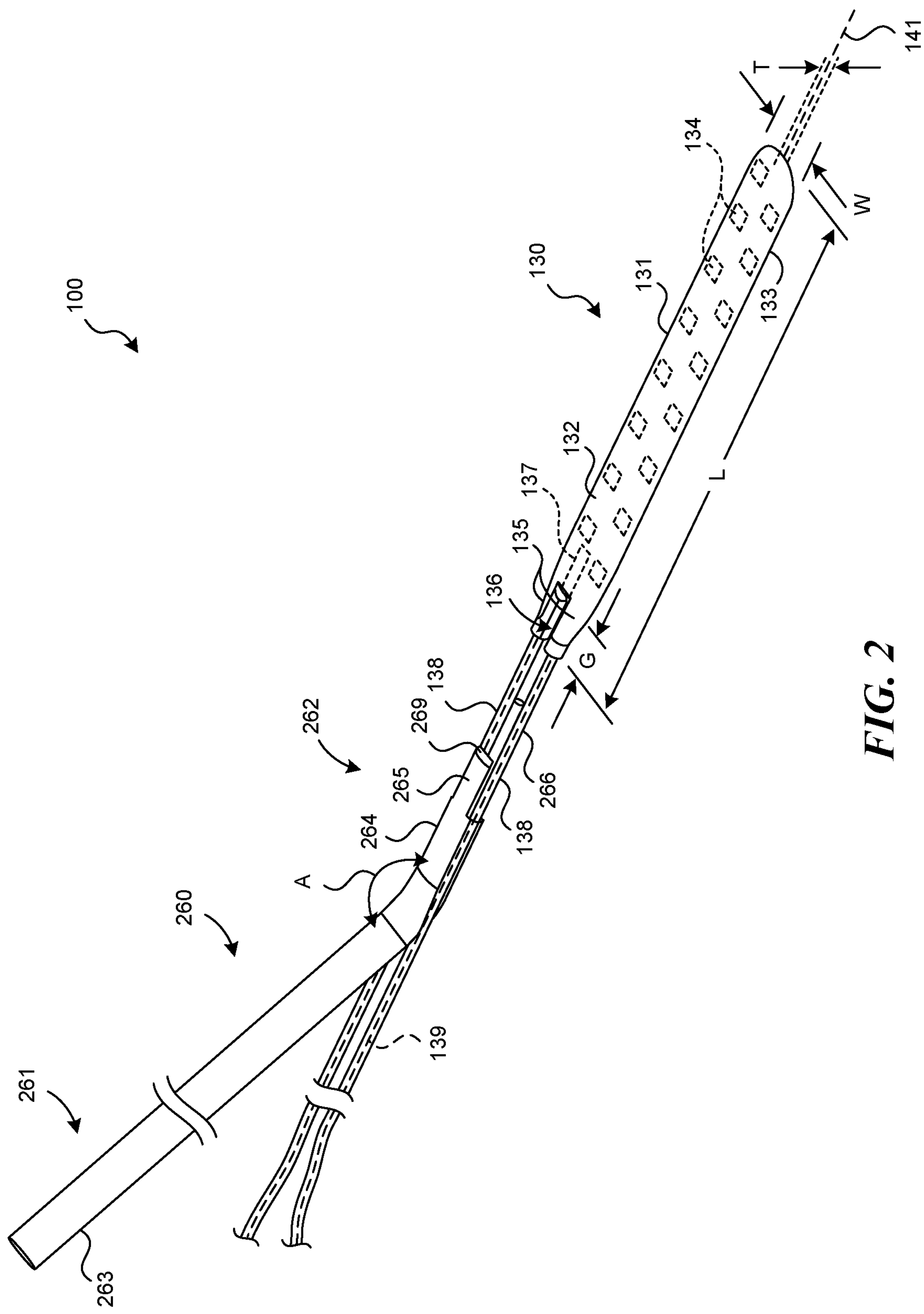
FIG. 2 is a partially schematic, isometric illustration of a representative signal delivery device and associated delivery tool configured in accordance with embodiments of the present technology.

FIG. 2 is a partially schematic, isometric illustration of a representative signal delivery device 130 and associated delivery tool 260. The signal delivery device 130 has a paddle configuration, and includes a paddle body 131 elongated along a longitudinal axis 141. The paddle body 131 has a length L along the longitudinal axis 141, a width W transverse to the longitudinal axis 141, and a thickness T transverse to the width W. In general, the paddle body 131 has a flattened configuration, with the thickness T less than the width W and the length L.

The paddle body 131 can have a first or upper surface 132 and a second or lower surface 133. The paddle body 131 carries one or more signal delivery electrodes 134 that are accessible from the lower surface 131. Accordingly, when the paddle body 131 is implanted so as to overlie the spinal cord, the exposed signal delivery electrodes 134 at the lower surface 133 are positioned to direct electrical signals towards the spinal cord.

Electrical current is directed to the paddle body 131 via one or more leads or lead tails 138, each of which carries one or more conductors 139 (shown schematically in FIG. 2). For example, in an embodiment shown in FIG. 2, the paddle body 131 can carry 16 signal delivery electrodes 134, which are supplied by a corresponding set of sixteen conductors 139, eight of which are housed in one lead or lead tail 138, and the remaining eight of which are housed in the other lead or lead tail 138. The lead tails 138 connect to the paddle body 131 at corresponding lead legs 135. The lead legs 135 can be separated by a gap 136 having a longitudinal dimension G generally aligned with the longitudinal axis 141. The paddle body 131 can further include an aperture 137 that extends along the longitudinal axis 141 in a direction distal from the gap 136. The gap 136 and the aperture 137 can facilitate engaging and disengaging the signal delivery device 130 and the delivery tool 260.

The delivery tool 260 can include a proximal region 261 having a handle 263 that the practitioner grasps to direct the motion of the signal delivery device 130. The delivery tool 260 can further include a distal region 262 having a connection portion 264 that releasably engages with the signal delivery device 130. The proximal region 261 can be inclined relative to the distal region 262 by a tool angle A so that the practitioner can comfortably grasp the handle 263 while moving the paddle body 131 in the desired direction.

In particular embodiments, the handle 263 can pivot relative to the distal region 262, so that the tool angle A is variable. For example, the delivery tool 260 can be formed from an injection molded plastic, and can be deliberately made more bendable at the juncture between the distal region 262 and the proximal region 261 than elsewhere along the length of the delivery tool 260. In a further particular aspect of this embodiment, the delivery tool 260 can have a reduced thickness at the juncture, e.g., in only the thickness direction T, so as to allow the tool angle A to change, without allowing the delivery tool 260 to bend or flex in other directions. An expected advantage of this arrangement is that the practitioner can change the tool angle A as the signal delivery device 130 is inserted and advanced, while still allowing the signal delivery device 130 to be advanced along the dura, rather than away from or into the dura. In a further particular aspect of this embodiment, the foregoing features are made simple, e.g., to reduce manufacturing costs and/or demands on the practitioner. Accordingly, the hinge between the distal region 262 and the proximal region 261 can be formed as an integral part of the delivery tool 260 (as described above), and can remain unfixed throughout the operation of the delivery tool 260. In other embodiments, the hinge can be more complex (e.g., can include a pivot pin), and/or can be releasably secured at any of a variety of desired tool angles A.

The connection portion 264 of the delivery tool 260 can include a central projection 265 that fits into the gap 136 between the lead legs 135 of the signal delivery device 130. By fitting snugly between the lead legs 135, the central projection 265 can give the practitioner control over the lateral motion of the signal delivery device 130 as it is inserted into the patient. In a particular embodiment, the central projection 265 can include opposing leading edges 269 (one of which is visible in FIG. 2) that extend beyond the longitudinal extent G of the gap 136 on the upper surface 132 and the lower surface 133. Accordingly, the central projection 265 can also provide a degree of control in the thickness direction T of the paddle body 131. In yet a further aspect of an embodiment shown in FIG. 2, the delivery tool 260 can also include an extension 266 that extends beyond the gap 136 and into the aperture 137 of the paddle body 131, to provide the practitioner with additional support and control of the paddle body 131. The connection portion 264 can include still further features that releasably interlock with corresponding features of the signal delivery device 130, as is described in further detail below with reference to FIGS. 3A and 3B.

Figure 3A:
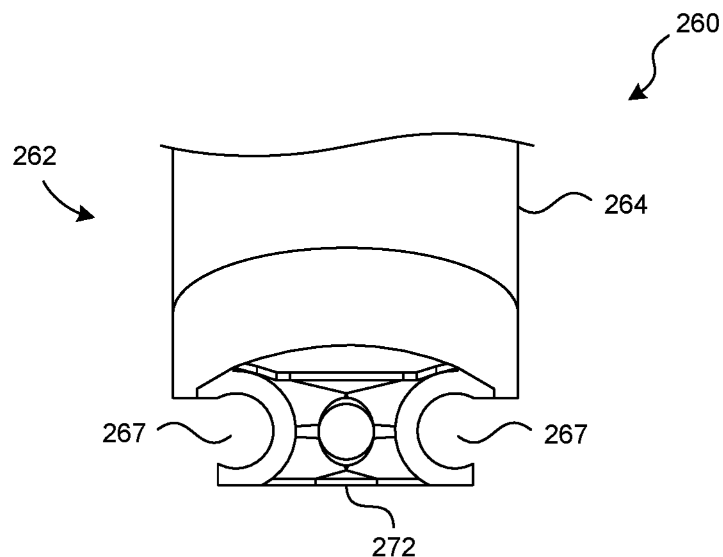
FIG. 3A is a partially schematic end view of an embodiment of the delivery tool shown in FIG. 2.
Figure 3B:
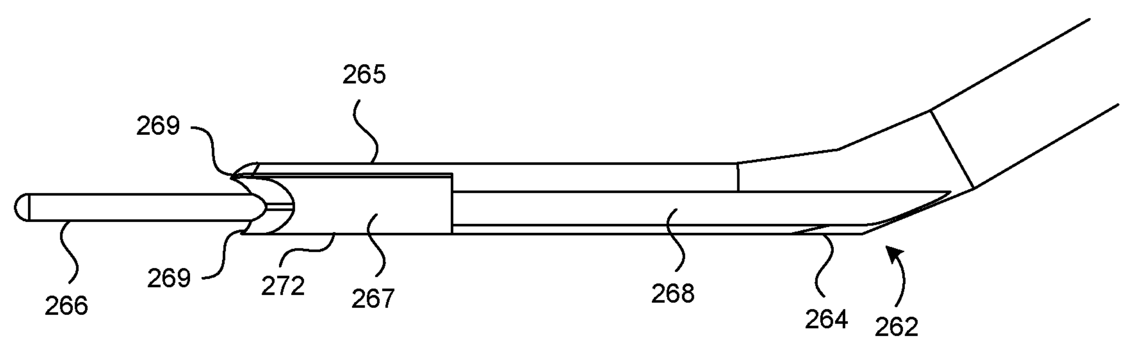
FIG. 3B is a partially schematic side view of an embodiment of the delivery tool shown in FIG. 2.

FIG. 3A is a partially schematic end view of the distal region 262 of an embodiment of the delivery tool 260 shown in FIG. 2, and FIG. 3B is a side view of the distal region 262. Referring to FIGS. 3A and 3B together, the distal region 262 can include two leg channels 267, each of which is positioned to receive a corresponding one of the lead legs 135 (FIG. 2). The leg channels 267 can be generally C-shaped in cross-section so that the lead legs 135 can slide into the leg channels 267. In a particular embodiment, the leg channel 267 can have an opening of at least 180° so that the leg can enter the leg channel 267 in a lateral direction or in an axial or longitudinal direction. In another embodiment, the opening into the leg channel 267 can have a circumferential extent of less than 180° so that the leg can either slide into the channel axially, or can be snapped into the channel laterally and can remain within the leg channels 267 without moving laterally outwardly away from the delivery tool 260. The diameter of one or more of the leg channels 267 can be selected to allow or inhibit axial motion of the lead legs 135. For example, if the diameter of the leg channel 267 is slightly greater than that of the lead leg 135 (resulting in a clearance fit), then the leg channel 267 can allow the lead leg 135 to slide into the leg channel axially and/or laterally. If the diameter of leg channel 267 is slightly less than that of the lead leg 135 (resulting in an interference fit), then the leg channel 267 inhibits axial motion of the lead leg 135, and the lead leg 135 will typically enter the leg channel 267 laterally rather than axially.

In a particular embodiment, the delivery tool 260 has a lower surface 272 shaped to reduce or eliminate the likelihood for the tool 260 to damage adjacent tissue. For example, the lower surface 272 can be recessed (e.g., in an upward direction in the view of FIGS. 3A and 3B) from the lower surface 133 of the paddle body 131 (FIG. 2). With such an arrangement, the tool lower surface 272 will not present a leading edge or forward facing step when inserted into the patient.

Referring now to FIG. 3B, the connection portion 262 can include two corresponding tail channels 268 (one of which is visible in FIG. 3B), each of which extends proximally from a corresponding one of the leg channels 267. The tail channels 268 can also be generally C-shaped in cross-section so as to receive the lead tails 138 (FIG. 2). The circumferential extent of the opening into the tail channel 268 can be either equal to or greater than 180° (so as to avoid lateral restriction) or less than 180° (so as to provide lateral restriction, generally in the manner discussed above with reference to the leg channels 267). The diameter of the tail channel 268 relative to the diameter of the lead tails 138 can also be selected to allow or inhibit axial motion of the lead tails 138, generally in the manner discussed above with reference to the leg channels 267. The leading edges 269 of the central portion 265 fit around the proximal end of the paddle body 131 (FIG. 2), as discussed above. The extension 266 extends into the aperture 137 (FIG. 2) of the lead body 131, as was also discussed above with reference to FIG. 2. The leading edges 269 can be outwardly chamfered or beveled so as not to present a steep forward facing step that might interfere with the practitioner's ability to smoothly advance and deliver the paddle body 131 into position within the patient. The leading edges 269 can be inwardly scarfed or chamfered to form a wedge shape that matches the proximal end of the paddle body 131.

Figure 4:
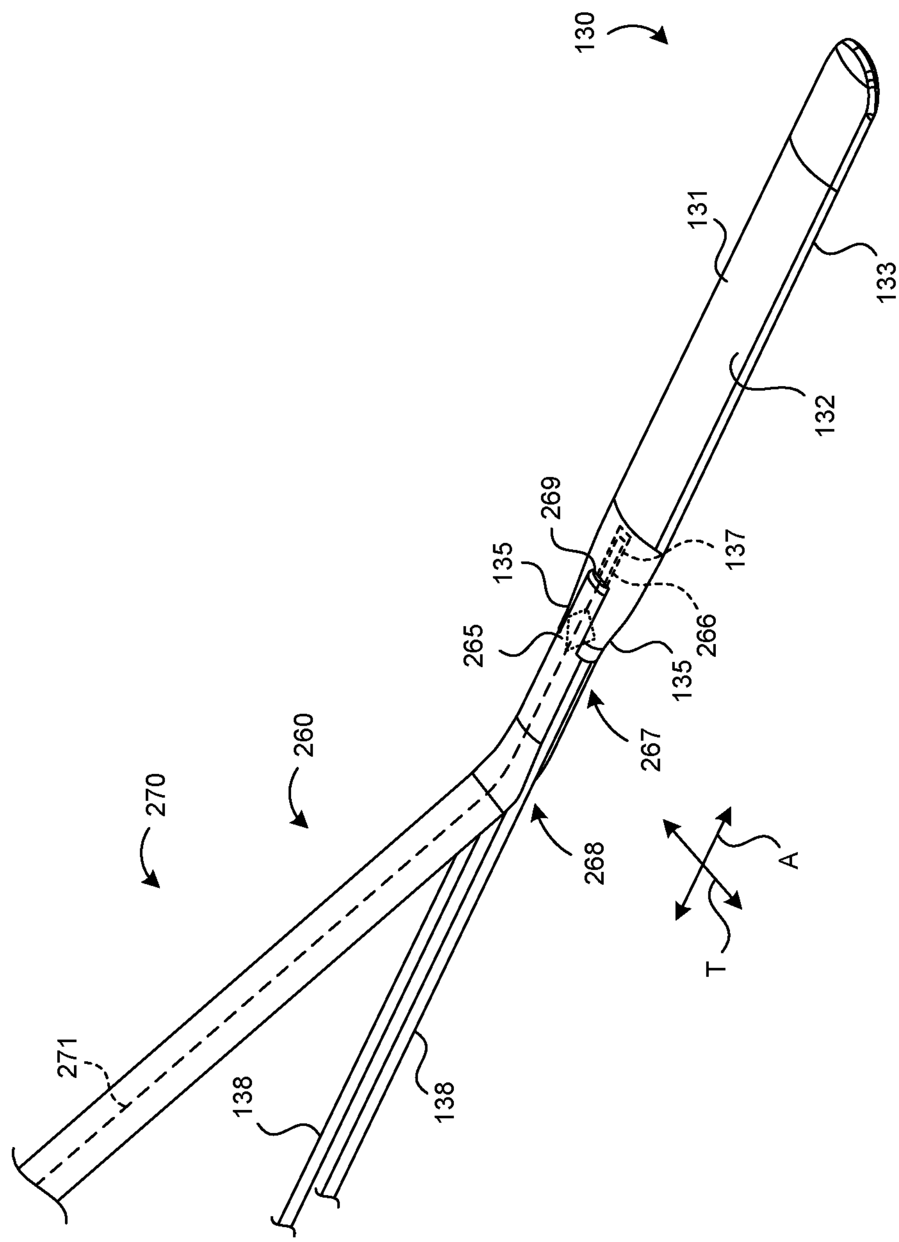
FIG. 4 is a partially schematic illustration of a delivery tool fully engaged with a signal delivery device in accordance with embodiments of the present technology.

FIG. 4 is a partially schematic, isometric illustration of the delivery tool 260 engaged with the signal delivery device 130. As shown in FIG. 4, the lead legs 135 of the signal delivery device 130 are received in the corresponding leg channels 267 of the delivery tool 260, and the lead tails 138 are received in the corresponding tail channels 268. The central portion 265 of the delivery tool 260 is located between the lead legs 135, with the leading edges 269 extending at least partially over the upper surface 132 and under the lower surface 133 of the paddle body 131. In this configuration, the practitioner can move the paddle body 131 into position and steer the paddle body 131 effectively, as a result of the positive and robust engagement between the delivery tool 260 and the signal delivery device 130. In addition, the tail channels 268 can keep the tails 138 in position so they are less likely to become twisted or entangled.

As is also shown in FIG. 4, the extension 266 of the delivery tool 260 extends into the aperture 137 of the paddle body 131. For example, the extension 266 can extend within the paddle body 131 by a distance ranging from about 10% to about 50% of the overall length of the paddle body 131. In further particular embodiments, the extension 266 can extend for about 25% of the length of the paddle body 131, as can the aperture 137.

In another aspect of this embodiment, the extension 266 can operate as part of an actuator 270 to disengage the paddle body 131 from the delivery tool 260 after the paddle body 131 is in its proper implanted position. For example, the extension 266 can be connected to an actuator cable 271 which is slideably carried in a corresponding channel or lumen of the delivery tool 260 to move axially, as indicated by arrow A. The practitioner can pull on the actuator cable 271 to place the extension 266 in a first (e.g., retracted) position, and push on the actuator cable 271 (with the channel or lumen preventing the actuator cable 271 from buckling), to place the extension 266 in a second (e.g., extended) position. In the extended position, the extension 266 pushes in a distal direction against the paddle body 131. This motion in turn forces the paddle body 131 away from the delivery tool 260.

If the leg channel 267 and/or the tail channel 268 have openings that extend circumferentially for less than 180°, the actuator 270 can be configured to push the signal delivery device (the lead legs and/or the tails) transversely or laterally outwardly from the delivery tool 260, as indicated by arrow T. For example, the actuator 270 can include a flexible element that expands laterally when actuated so as to force the lead legs and/or lead tails laterally outwardly from the corresponding channels in which they are housed. In a particular embodiment, the actuator 270 can split into a diamond shape (as indicated in dotted lines in FIG. 4) so as to exert a transverse or lateral disengaging force on the lead legs 135.

In still further embodiments, the actuator 270 can be eliminated. For example, the practitioner can partially insert the paddle body 131 into the spinal canal, or can fully insert the paddle body 131 into the spinal canal and then partially withdraw the paddle body. In either case, the proximal portion of the paddle body 131 can be exposed while the practitioner disengages the delivery tool 260 manually. For example, the practitioner can pop the lead tails 138 out of their corresponding tail channels 268 and remove the delivery tool 260 from engagement with the paddle body 131. The practitioner can then manually push the paddle body 131 over the final distance necessary to place it at its final implanted position.

Figure 5A:
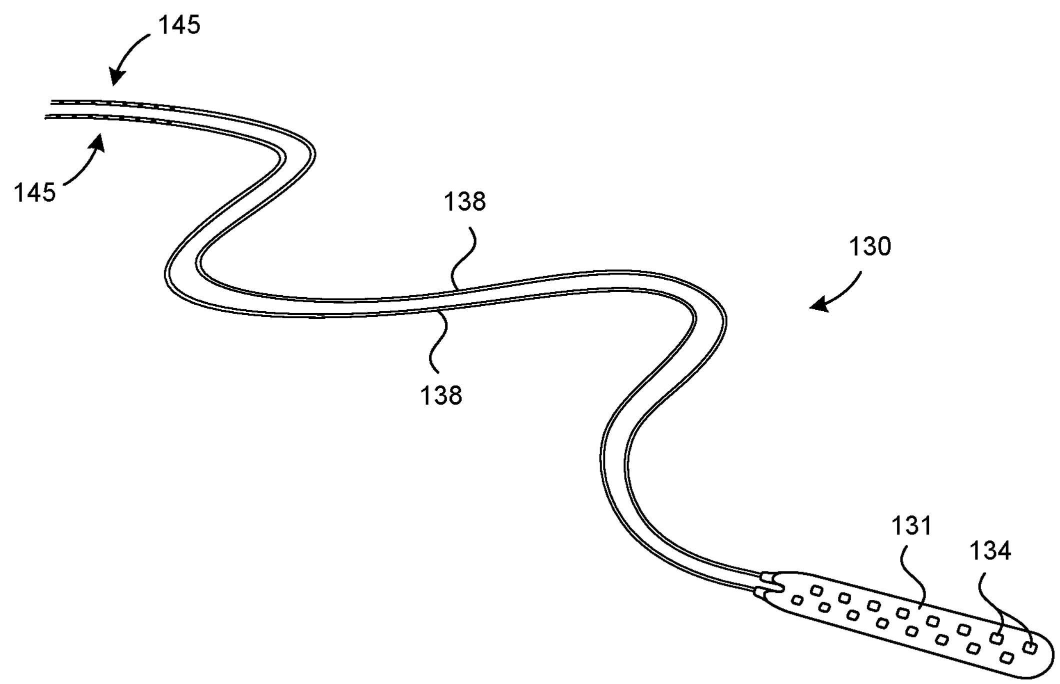
FIG. 5A is a partially schematic, isometric illustration of a signal delivery device having a paddle configuration in accordance with embodiments of the present technology.
Figure 5B:
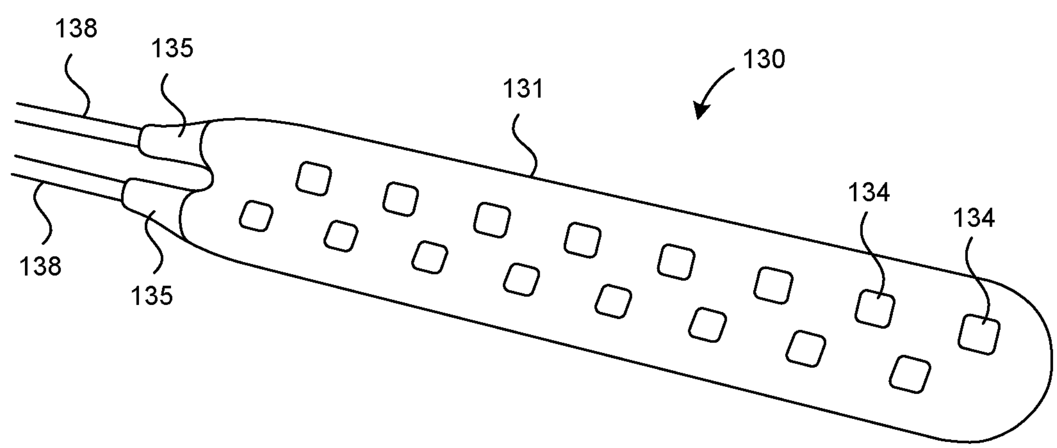
FIG. 5B is an enlarged illustration of a portion of the signal delivery device shown in FIG. 5A.
Figure 5C:
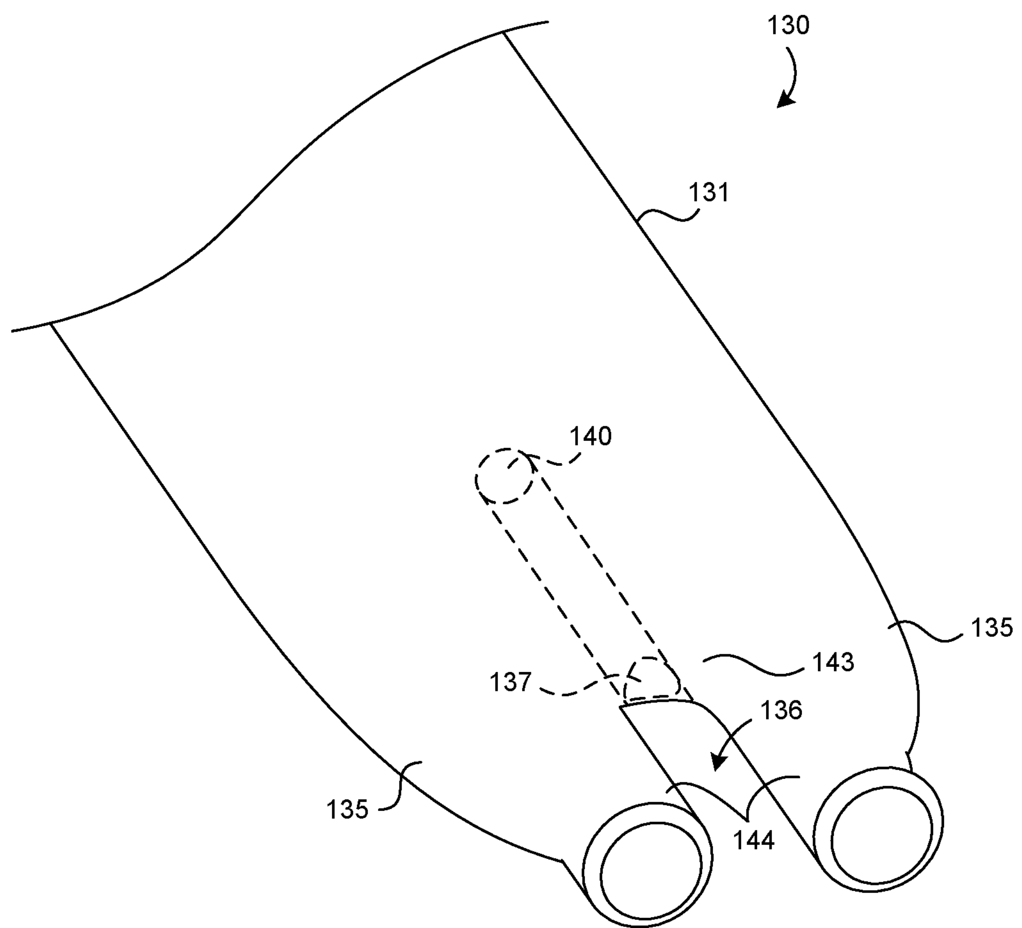
FIG. 5C is a partially schematic, rear view of a portion of the signal delivery device shown in FIGS. 5A and 5B.

FIGS. 5A-5C further illustrate an embodiment of the signal delivery device 130. FIG. 5A illustrates the overall signal delivery device 130, including the paddle body 131 carrying the signal delivery electrodes 134 and the associated leads 138. Corresponding proximal contacts 145 provide an electrical connection between the conductors within the leads 138, and the signal generation circuitry of the IPG 101 (FIG. 1A). FIG. 5B is an enlarged illustration of the paddle body 131, the lead legs 135, and the distal portions of the lead tails 138.

FIG. 5C is an enlarged illustration of the proximal portion of the paddle body 131, illustrating the gap 136 between the lead legs 135. Each of the lead legs 135 can include an inwardly facing surface 144 that is received in the corresponding leg channel 267 of the signal delivery device. The paddle body 131 includes a proximally facing surface 143 in which the aperture 137 is positioned. The aperture 137 can have a distal wall 140. Accordingly, the extension 266 (described above) can be actuated so as to move in a distal direction against the distal wall 140 to disengage the signal delivery device 130 from the delivery tool 260.

Figure 6:
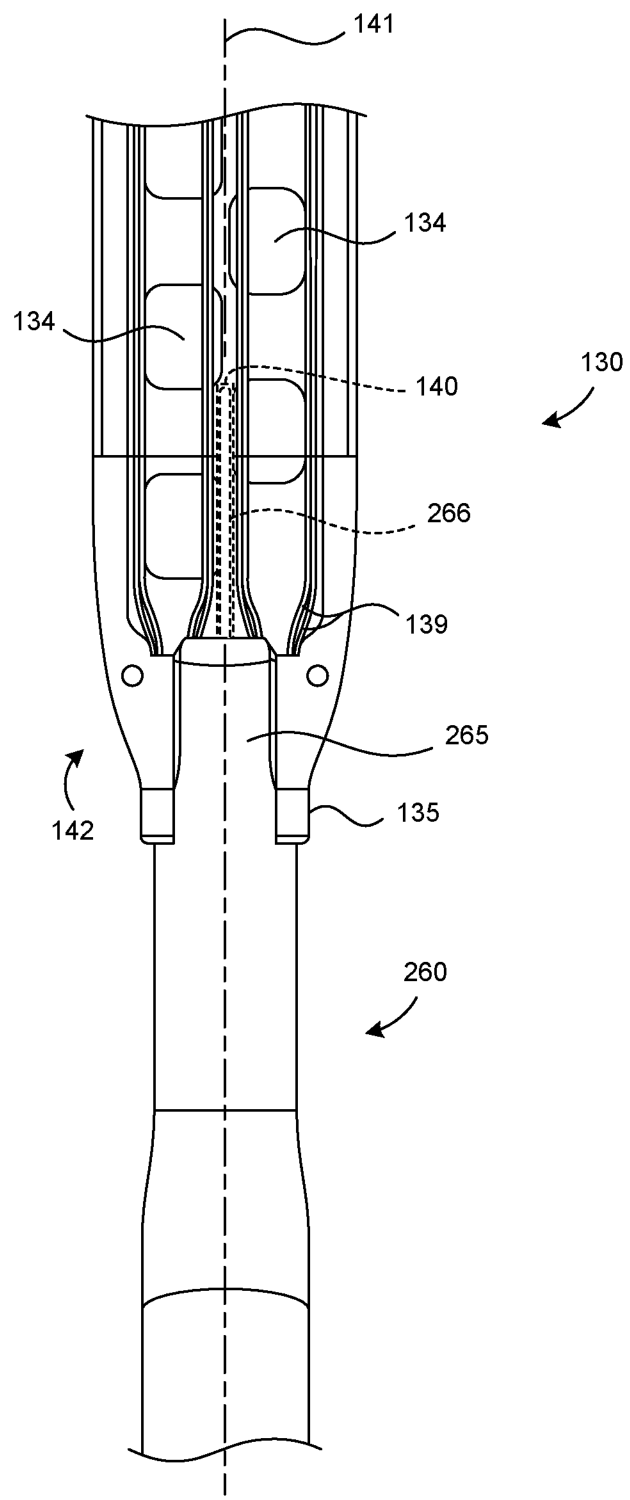
FIG. 6 is a partially schematic, isometric illustration of a delivery tool engaged with a signal delivery device in accordance with embodiments of the present technology.

FIG. 6 is a partially schematic top view of the signal delivery device 130 and the delivery tool 260, shown in an engaged configuration. Accordingly, the extension 266 of the delivery tool 260 is positioned within the aperture 137 of the signal delivery device 130, proximate to the distal wall 140.

The paddle body 131 can include a tapering portion 142 that tapers inwardly toward the longitudinal axis 141 in a proximal direction. While the internal extension 266 may extend beyond the tapering portion 142, the external portions of the delivery tool, in this embodiment, do not extend beyond the tapering portion 142. For example, the central projection 265, which is positioned external to the paddle body 131, terminates within the length of the tapering portion 142. As discussed further below with reference to FIG. 7, this approach can reduce the profile of the combined paddle body 131 and delivery tool 260 to make delivering the lead body smoother.

Figure 7:
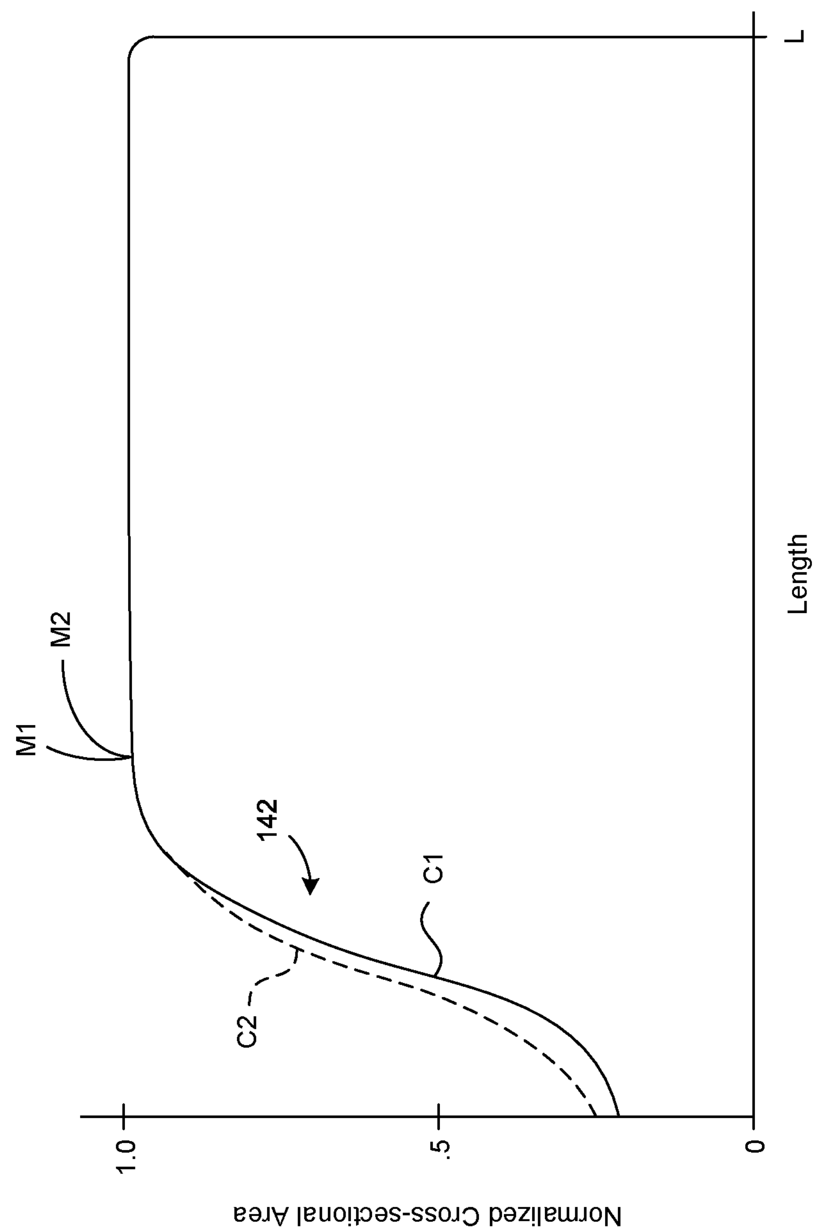
FIG. 7 is a graph illustrating a normalized cross-sectional area of a signal delivery device, with and without an associated delivery tool, as a function of length, in accordance with embodiments of the present technology.

FIG. 7 is a graph illustrating the cross-sectional area of the signal delivery device 130 over its length L (e.g., the length of the paddle body 131, including the lead legs 135, but not including the lead tails 138). The cross-sectional area is taken normal to the longitudinal axis 141 (FIG. 2) of the signal delivery device 130 and so includes the extent of the signal delivery device in the widthwise direction W and thickness direction T (FIG. 2). The cross-sectional area has been normalized so that a value of 1.0 corresponds to the maximum cross-sectional area of the signal delivery device along its length L. Curve C1 corresponds to the normalized cross-sectional area of the lead body alone, without the delivery tool 260. Accordingly, the cross-sectional area increases over the tapering portion 142, reaches a first maximum M1, and remains constant until near the distal end of the lead body, at which point it rapidly decreases to zero. When the delivery tool 260 is engaged with the lead body, as indicated by curve C2, the combined cross-sectional area is increased, but only over the tapering portion 142. Accordingly, curve C2 has a second maximum M2 that is the same as the maximum M1 of the lead body alone. An advantage of this arrangement is that the presence of the signal delivery device is less likely to interfere with inserting the paddle body, and can be less likely to widen the incision made in the patient (to receive the paddle body) as the paddle body is inserted.

Figure 8A:
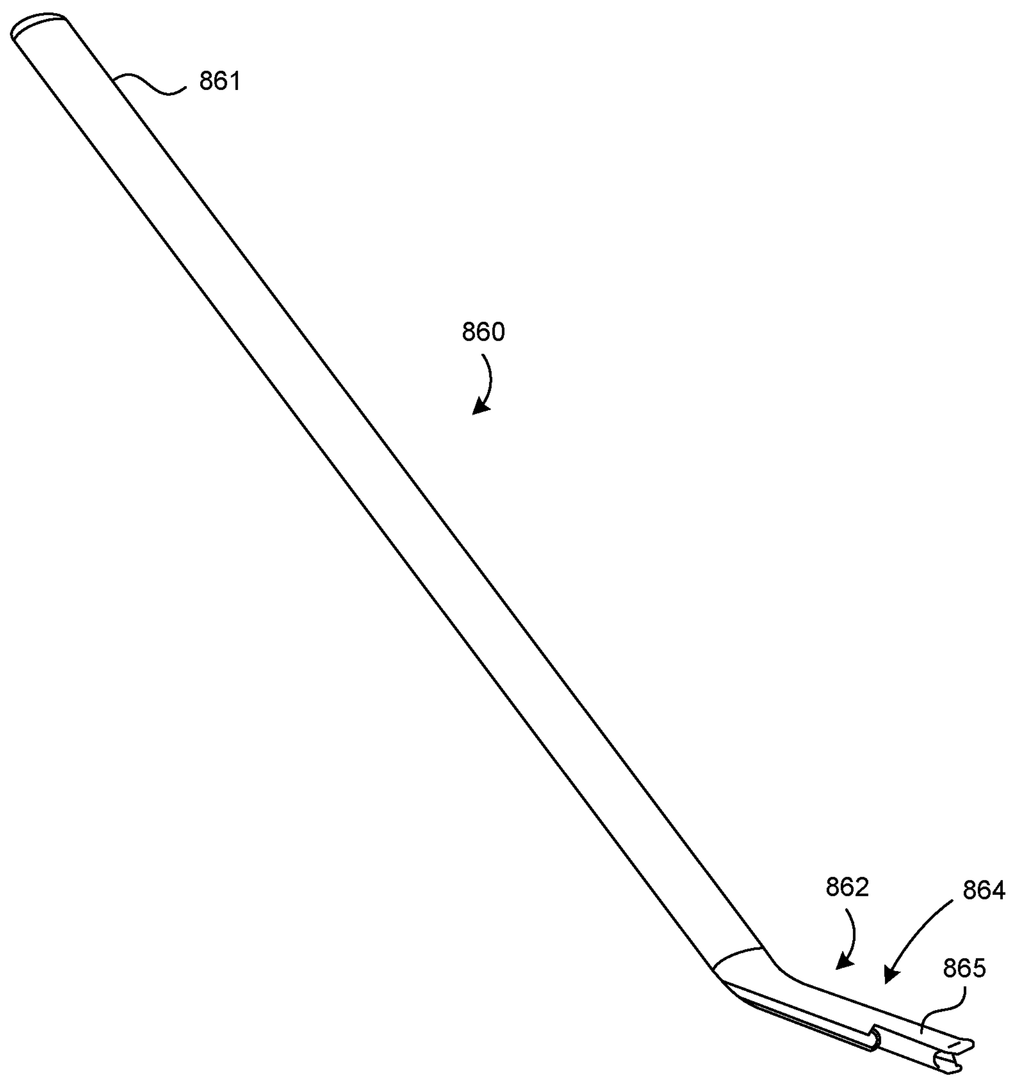
FIG. 8A is a partially schematic illustration of a delivery tool configured in accordance with another embodiment of the present technology.
Figure 8B:
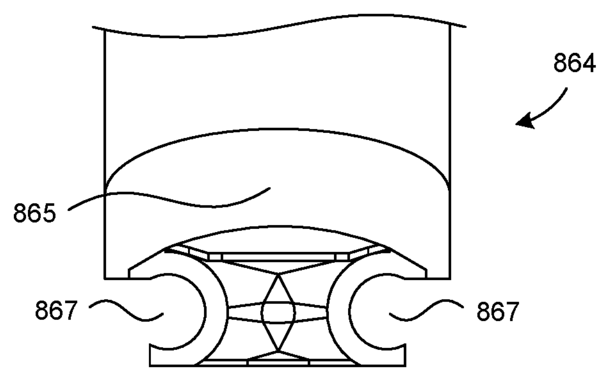
FIG. 8B is a partially schematic end view of an embodiment of the delivery tool shown in FIG. 8A.
Figure 8C:
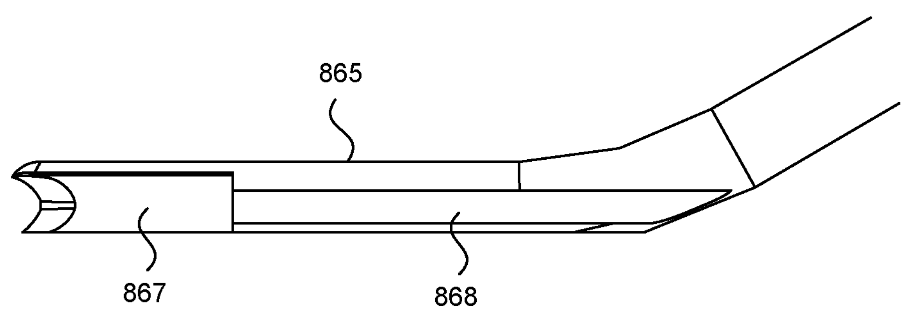
FIG. 8C is a partially schematic side view of an embodiment of the delivery tool shown in FIGS. 8A and 8B.

FIGS. 8A-8C illustrate a delivery tool 860 configured in accordance with another embodiment of the present technology. As shown in FIG. 8A, the delivery tool 860 can include a proximal region 861, and a distal region 862 having a connection portion 864 with a central portion 865. As shown in FIGS. 8B and 8C, the central portion 865 can have a leg channel 867, and a tail channel 868. In this embodiment, the delivery tool 860 does not include an extension or actuator, which were discussed above with reference to FIGS. 2-6. Accordingly, this embodiment can be simpler to manufacture than an embodiment that includes these features. Conversely, an embodiment that includes the extension and/or actuator can be simpler to disengage from the lead body, and may provide an additional level of control over the motion of the lead body.

One feature of several of the embodiments described above is that they can include elements that facilitate a positive engagement between the lead body and the delivery tool. For example, the leg channels 267, the tail channels 268, the extension 266, and the central projection 265 each provide one or more surfaces that are positively engaged with corresponding surfaces of the signal delivery device 130. At the same time, these features do not increase the maximum cross-sectional area of the signal delivery device, as discussed above with reference to FIG. 7. To the extent the foregoing features do increase the cross-sectional shape of the combined signal delivery device/delivery tool, the increase is in a region toward the proximal end of the lead body where the lead body is tapered and where the increase in cross-sectional area has limited or negligible effect.

Still further, the delivery tool can be shaped to reduce (e.g., minimize) the potential for catching on or otherwise damaging the adjacent tissue as it advances the signal delivery device into the patient. For example, the delivery tool can include chamfered, sloped, and/or recessed edges and surfaces to aid the practitioner in smoothly advancing the signal delivery device.

The devices described above may be used to deliver a number of suitable therapies, e.g., paresthesia-based therapies and/or paresthesia-free therapies. One example of a paresthesia-free SCS therapy system is a "high frequency" SCS system. High frequency SCS systems can inhibit, reduce, and/or eliminate pain via waveforms with high frequency elements or components (e.g., portions having high fundamental frequencies), generally with reduced or eliminated side effects. Such side effects can include unwanted paresthesia, unwanted motor stimulation or blocking, unwanted pain or discomfort, and/or interference with sensory functions other than the targeted pain. In a representative embodiment, a patient may receive high frequency therapeutic signals with at least a portion of the therapy signal at a frequency of from about 1.5 kHz to about 100 kHz, or from about 1.5 kHz to about 50 kHz, or from about 3 kHz to about 20 kHz, or from about 5 kHz to about 15 kHz, or at frequencies of about 8 kHz, 9 kHz, or 10 kHz. These frequencies are significantly higher than the frequencies associated with conventional "low frequency" SCS, which are generally below 1,200 Hz, and more commonly below 100 Hz. Accordingly, modulation at these and other representative frequencies (e.g., from about 1.5 kHz to about 100 kHz) is occasionally referred to herein as "high frequency stimulation," "high frequency SCS," and/or "high frequency modulation." Further examples of paresthesia-free SCS systems are described in U.S. Patent Publication Nos. 2009/0204173 and 2010/0274314, the respective disclosures of which are herein incorporated by reference in their entireties.

From the foregoing, it will be appreciated that specific embodiments of the present technology have been described herein for purposes of illustration, but that various modifications may be made without deviating from the present technology. For example, the signal delivery device may have more or fewer signal delivery contacts or electrodes than are specifically illustrated above. The signal delivery tool can have actuator mechanisms different than those specifically described above. Several of the elements identified above with separate reference numbers maybe integrated to form a single unit. For example, the lead body and lead legs may be formed as a single, integral unit.

Certain aspects of the technology described in the context of particular embodiments may be combined or eliminated in other embodiments. For example, as discussed above, the actuator may be eliminated in some embodiments. In other embodiments, the signal delivery tool can include fewer than all the features described above. In particular, the signal delivery device can include a leg channel, but no tail channel. In another embodiment, the extension can be eliminated. Accordingly, the signal delivery tool can include any of a number of suitable combinations of the foregoing features, depending upon the particular embodiment. Further, while advantages associated with certain embodiments of the technology have been described in the context of those embodiments, other embodiments may also exhibit such advantages, and not all embodiments need necessarily exhibit such advantages to all within the scope of the present technology. Accordingly, the disclosure and associated technology can encompass other embodiments not expressly shown or described herein.

To the extent any materials incorporated by reference herein conflict with the present disclosure, the present disclosure controls.

I claim:

1. A patient therapy system, comprising:
a signal delivery paddle including:
a paddle body having an upper surface and a lower surface facing away from the upper surface, the paddle body carrying a plurality of signal delivery electrodes and having two lead legs projecting in a proximal direction and separated by a gap; and
two lead tails, each extending from a corresponding one of the lead legs and each carrying at least one conductor electrically connected to a corresponding one of the signal delivery electrodes; and
a delivery tool removably coupleable to the signal delivery paddle, the delivery tool including:
a proximal handle;
a distal connection portion connected to the proximal handle and having:
a central projection sized to fit within the gap between the two legs of the signal delivery paddle;
two outward-opening C-shaped leg channels, each positioned along the central projection to receive a corresponding one of the lead legs;
two outward-opening C-shaped tail channels, each positioned along the distal connection portion to receive a corresponding one of the lead tails; and
an actuator positioned to move between a first position in which the distal connection portion is engaged with the signal delivery paddle, and a second position in which the signal delivery paddle is forced away from the distal connection portion.

2. The system of claim 1 wherein the paddle body includes a blind aperture, and wherein the distal connection portion of the delivery tool includes an extension positioned to be releasably received in the aperture.

3. The system of claim 2 wherein the extension is carried by the central projection.

4. The system of claim 2 wherein the extension is a portion of the actuator.

5. The system of claim 1 wherein the paddle body alone has a paddle body length, is elongated along a longitudinal axis, and has a first cross-sectional area distribution along the longitudinal axis, the first cross-sectional area distribution including a first maxima, and wherein the paddle body and the delivery tool together have a combined second cross-sectional area distribution along the longitudinal axis, the second cross-sectional area distribution including a second maxima over the length of the paddle body that is no greater than the first maxima.

6. The system of claim 1 wherein the delivery tool has no forward facing steps over the length of the paddle body.

7. The system of claim 1 wherein the delivery tool has at least one forward facing edge over the length of the paddle body.

8. The system of claim 1 wherein a diameter of at least one of the leg channels of the delivery tool is greater than a diameter of a corresponding at least one lead leg of the signal delivery paddle.

9. The system of claim 1 wherein a diameter of at least one of the leg channels of the delivery tool is less than a diameter of a corresponding at least one lead leg of the signal delivery paddle.

10. The system of claim 1 wherein the central portion has a leading edge that fits over the upper surface of the paddle body.

11. The system of claim 1 wherein the central portion has a leading edge that fits under the lower surface of the paddle body.

12. The system of claim 1 wherein the central portion has a first leading edge that fits over the upper surface of the paddle body and a second leading edge that fits under the lower surface of the paddle body.

* * * * *